United States Patent
Martin et al.

(10) Patent No.: US 10,238,381 B1
(45) Date of Patent: *Mar. 26, 2019

(54) AUTOMATED NEEDLE LOADER

(71) Applicant: Ethicon Endo-Surgery, LLC, Guaynabo, PR (US)

(72) Inventors: David T. Martin, Milford, OH (US); Benjamin D. Dickerson, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 85 days.

This patent is subject to a terminal disclaimer.

(21) Appl. No.: 15/180,455

(22) Filed: Jun. 13, 2016

Related U.S. Application Data

(63) Continuation of application No. 13/793,048, filed on Mar. 11, 2013, now Pat. No. 9,370,354.

(51) Int. Cl.
*A61B 17/06* (2006.01)
*A61B 17/062* (2006.01)
*A61B 17/04* (2006.01)

(52) U.S. Cl.
CPC ........ *A61B 17/062* (2013.01); *A61B 17/0469* (2013.01); *A61B 17/06004* (2013.01); *A61B 2017/0498* (2013.01); *A61B 2017/06028* (2013.01); *A61B 2017/06042* (2013.01)

(58) Field of Classification Search
CPC ............ A61B 17/0482; A61B 17/0483; A61B 17/062; A61B 17/0625; A61B 17/06061; A61B 2017/0608; A61B 2017/06142; A61B 2017/0479; A61B 19/0288; A61B 19/0262; A61B 17/06161; A61B 17/06114–17/06128; B65D 85/24; B65D 83/02

See application file for complete search history.

(56) References Cited

U.S. PATENT DOCUMENTS

| | | |
|---|---|---|
| 3,598,281 A | 8/1971 | Watermeier |
| 5,437,681 A | 8/1995 | Meade et al. |
| 5,478,345 A | 12/1995 | Stone et al. |
| 5,540,706 A | 7/1996 | Aust et al. |
| 5,755,729 A | 5/1998 | de la Torre et al. |
| 5,792,135 A | 8/1998 | Madhani et al. |
| 5,814,069 A | 9/1998 | Schulze et al. |

(Continued)

OTHER PUBLICATIONS

U.S. Appl. No. 61/355,832, filed Apr. 17, 2010.
U.S. Appl. No. 61/413,680, filed Nov. 15, 2010.

*Primary Examiner* — Eric Rosen
*Assistant Examiner* — Mikail Mannan
(74) *Attorney, Agent, or Firm* — Frost Brown Todd LLC

(57) ABSTRACT

An apparatus for loading suture needles into a surgical instrument comprises a body, a first movable member, an engagement feature, and a needle. The body has a channel configured to receive a surgical instrument. The engagement feature is configured to open a cover of a surgical instrument upon insertion of a surgical instrument into the channel of the body. The first movable member is configured to deliver the suture needle to a surgical instrument after a surgical instrument has been inserted into the channel and the cover has been opened. The apparatus may further comprise a second movable member configured to facilitate delivery of the needle to a surgical instrument in conjunction with the first movable member.

20 Claims, 34 Drawing Sheets

(56) References Cited

U.S. PATENT DOCUMENTS

| | | |
|---|---|---|
| 5,817,084 A | 10/1998 | Jensen |
| 5,878,193 A | 3/1999 | Wang et al. |
| 5,908,248 A | 6/1999 | Scirica et al. |
| 6,056,771 A | 5/2000 | Proto |
| 6,071,289 A | 6/2000 | Stefanchik et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 6,783,537 B1 | 8/2004 | Kuhr et al. |
| 6,923,819 B2 | 8/2005 | Meade et al. |
| 7,524,320 B2 | 4/2009 | Tierney et al. |
| 7,628,796 B2 | 12/2009 | Shelton, IV et al. |
| 7,691,098 B2 | 4/2010 | Wallace et al. |
| 7,770,365 B2 | 8/2010 | Enriquez et al. |
| 7,806,891 B2 | 10/2010 | Nowlin et al. |
| 7,824,401 B2 | 11/2010 | Manzo et al. |
| 7,862,572 B2 | 1/2011 | Meade et al. |
| 7,976,555 B2 * | 7/2011 | Meade ............... A61B 17/0469 206/338 |
| 8,307,978 B2 | 11/2012 | Kirsch et al. |
| 8,702,732 B2 | 4/2014 | Woodard et al. |
| 9,125,646 B2 | 9/2015 | Woodard et al. |
| 9,168,037 B2 | 10/2015 | Woodard et al. |
| 9,370,354 B1 | 6/2016 | Martin et al. |
| 2007/0162052 A1 | 7/2007 | Hashimoto et al. |
| 2010/0100125 A1 | 4/2010 | Mahadevan |
| 2013/0282027 A1 | 10/2013 | Woodard et al. |

\* cited by examiner

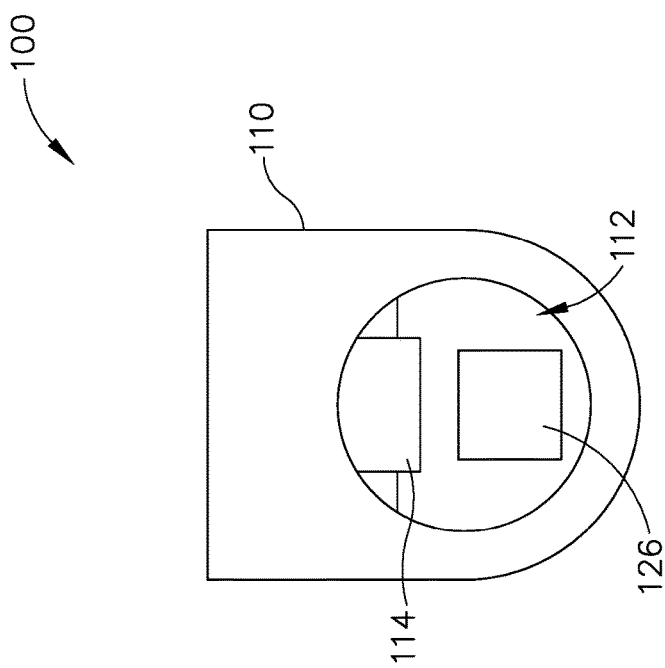

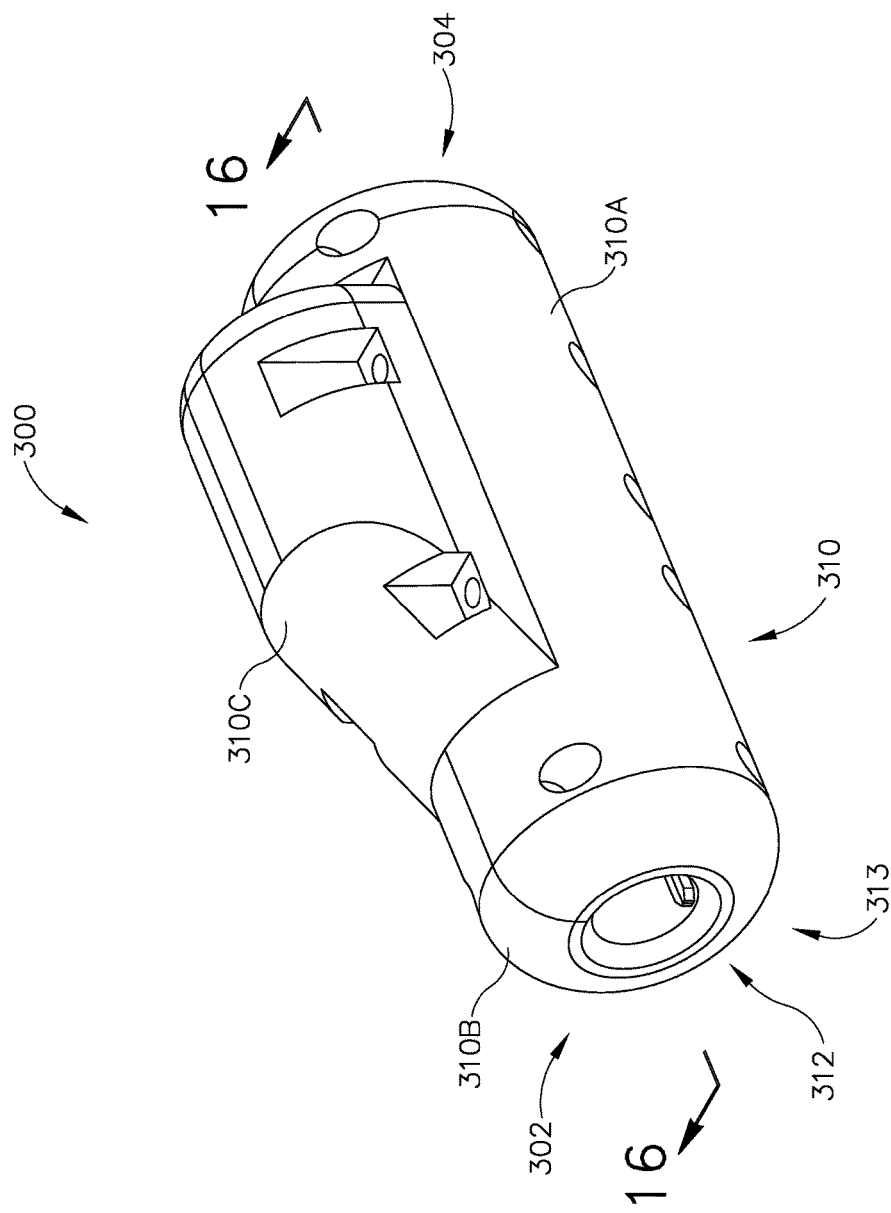

AUTOMATED NEEDLE LOADER

This application is a continuation of U.S. Non-Provisional application Ser. No. 13/793,048, filed Mar. 11, 2013, entitled "Automated Needle Loader," published as U.S. Pat. No. 9,370,354.

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laprascopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio.

Additional suturing instruments are disclosed in U.S. Pat. No. 5,437,681, entitled "Suturing Instrument with Thread Management," issued Aug. 1, 1995, the disclosure of which is incorporated by reference herein; U.S. Pat. No. 5,540,706, entitled "Surgical Instrument," issued Jul. 30, 1996, the disclosure of which is incorporated by reference herein; U.S. Pat. No. 6,923,819, entitled "Apparatus and Method for Surgical Suturing with Thread Management," issued Aug. 2, 2005, the disclosure of which is incorporated by reference herein; U.S. Pat. No. 6,071,289, entitled "Surgical Device for Suturing Tissue," issued Jun. 6, 2000, the disclosure of which is incorporated by reference herein; U.S. Pat. No. 7,628,796, entitled "Surgical Suturing Apparatus with Anti-Backup System," issued Dec. 8, 2009, the disclosure of which is incorporated by reference herein; U.S. Pat. No. 7,862,572, entitled "Apparatus and Method for Minimally Invasive Suturing," issued Jan. 4, 2011, the disclosure of which is incorporated by reference herein; U.S. Pat. No. 7,976,555, entitled "Apparatus and Method for Minimally Invasive Suturing," issued Jul. 12, 2011, the disclosure of which is incorporated by reference herein; U.S. Pub. No. 2011/0313433, entitled "Laparoscopic Suture Device with Asynchronous In-Line Needle Movement," filed Jun. 9, 2011, now U.S. Pat. No. 9,168,037, issued Oct. 27, 2015, the disclosure of which is incorporated by reference herein; U.S. patent application Ser. No. 13/449,494, entitled "Laparoscopic Suturing Instrument with parallel Concentric Shaft Pairs," filed Apr. 18, 2012, now U.S. Pat. Pub. No. 2013/0282027, published Oct. 24, 2013, now U.S. Pat. No. 9,451,946, issued Sep. 27, 2016, the disclosure of which is incorporated by reference herein; and U.S. Provisional Patent Application No. 61/355,832, entitled "Laparoscopic Suture Device," filed Jun. 17, 2010, the disclosure of which is incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; U.S. Pub. No. 2010/0100125, entitled "Suture Needle and Suture Assembly," published Apr. 22, 2010, now abandoned, the disclosure of which is incorporated by reference herein; U.S. Provisional Application Ser. No. 61/413,680, filed Nov. 15, 2010, entitled "Custom Needle for Suture Instrument," the disclosure of which is incorporated by reference herein; U.S. patent application Ser. No. 13/295,186, entitled "Needle for Laparoscopic Suturing Instrument," filed on Nov. 14, 2011 now U.S. Pat. No. 9,125,646, issued Sep. 8, 2015, the disclosure of which is incorporated by reference herein; and U.S. patent application Ser. No. 13/295,203, entitled "Laparoscopic Suturing Instrument with Dual-Action Needle Graspers," filed on Nov. 14, 2011, now U.S. Pat. No. 8,702,732, issued Apr. 22, 2014, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9 depicts a front elevational view of the needle loader of FIG. 8,

FIG. 14 depicts a perspective view of another exemplary alternative needle loader suitable for use with the instrument of FIG. 1;

Figure 1:
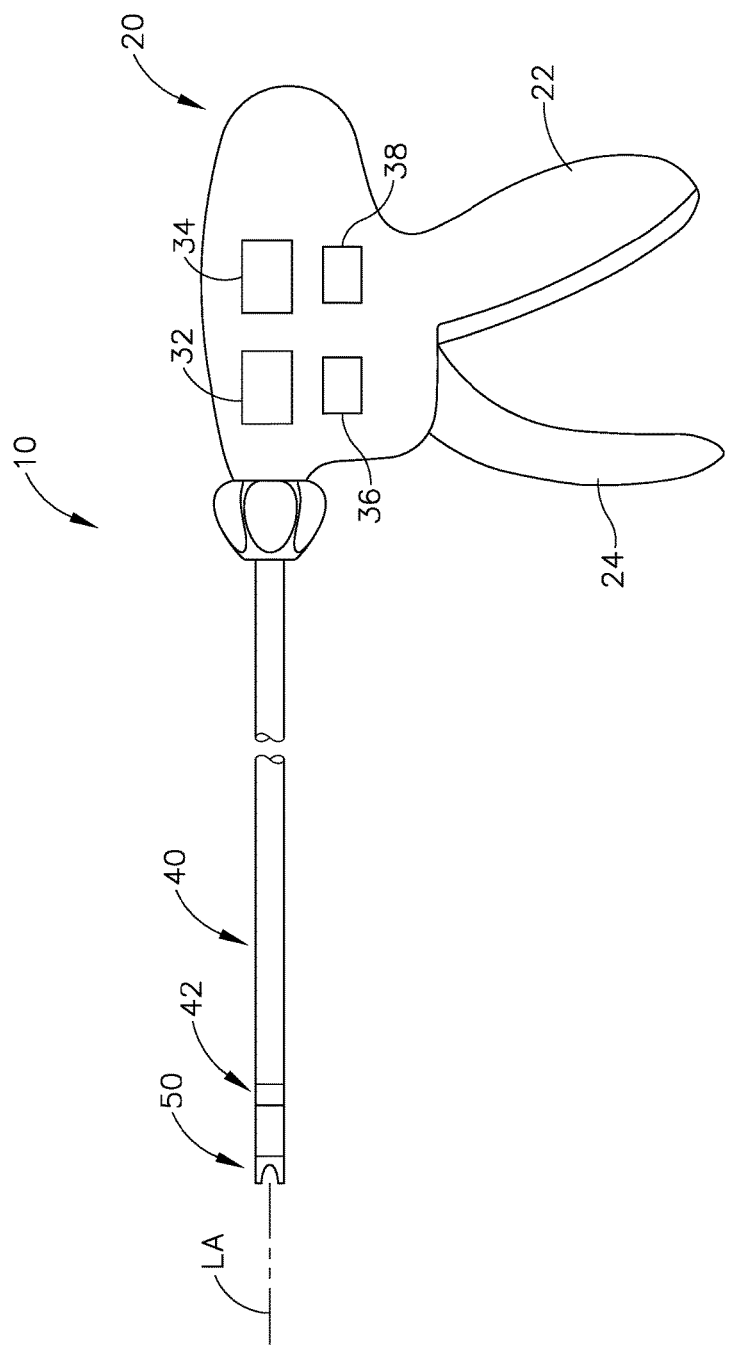
FIG. 1 depicts a schematic elevational view of an exemplary suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Suturing Instrument

FIG. 1 shows an exemplary laparoscopic suturing instrument (10), which may be used to suture tissue in numerous kinds of surgical procedures. Instrument (10) of this example includes a handle portion (20), a shaft (40) extending distally from handle portion (20), and an end effector (50) that is joined to shaft (40) by a joint (42). Handle portion (20) includes a grip (22) and a trigger (24), which is pivotable relative to grip (22) to actuate end effector (50) as will be described in greater detail below. In some versions, shaft (40) and end effector (50) are configured to fit through a conventional trocar. It should therefore be understood that instrument (10) may be used in minimally invasive procedures. Of course, instrument (10) may be used through passageways other than trocars (e.g., through a thoracotomy, etc.) or in open procedures if desired.

In the present example, shaft (40) is rotatable to position end effector (50) at various angular orientations about the longitudinal axis (LA) defined by shaft (40). To that end, handle portion (20) includes a rotation control (32). It should be understood that rotation control (32) may take a variety of forms, including but not limited to a knob, a dial, a grip at the proximal end of shaft (40), etc. Various suitable forms that rotation control (32) may take will be apparent to those of ordinary skill in the art in view of the teachings herein. In addition to providing rotation of end effector (50), instrument (10) also provides articulation of end effector (50). In particular, joint (42) at the distal end of shaft (40) enables end effector (50) to pivotally deflect away from the longitudinal axis (LA) defined by shaft (40) to achieve various articulation angles. It should be understood that these various articulation angles may be achieved at any of the various angular orientations provided through rotation control (32). Handle portion (20) further includes an articulation control (34), which may include any suitable component such as a knob, a dial, a lever, a slider, etc. Various suitable forms that articulation control (34) may take will be apparent to those of ordinary skill in the art in view of the teachings herein. Similarly, various suitable components and configurations that may be used to provide articulation of end effector (50) at joint (42) in response to actuation of articulation control (34) will be apparent to those of ordinary skill in the art in view of the teachings herein. By way of example only, articulation may be provided in accordance with at least some of the teachings of U.S. Pat. No. 7,862,572, the disclosure of which is incorporated by reference herein.

In some versions, handle portion (20) includes a powered motive source (36). Powered motive source (36) may comprise a motor, a solenoid, and/or any other suitable type of powered motive source. Powered motive source (36) may be used to drive end effector (50) as will be described in greater detail below, to rotate shaft (40), to articulate end effector (50) at joint (42), and/or to provide any other suitable type of operation. It should also be understood that handle portion (20) may include an integral power source (38). By way of example only, integral power source (38) may comprise a rechargeable battery coupled with powered motive source (36). Alternatively, in versions of instrument (10) where at least one component receives electrical power, such electrical power may be provided by an external source that is coupled with instrument (10) via wire, via inductive coupling, or otherwise. It should be understood that versions of instrument (10) having powered motive source (36) and/or integral power source (38) may have additional associated components, including but not limited to transmission components, clutch components, sensors, a control module, etc. Various suitable components and combinations thereof will be apparent to those of ordinary skill in the art in view of the teachings herein. It should also be understood that instrument (10) may simply lack powered motive source (36) and/or power source (38).

Figure 2:
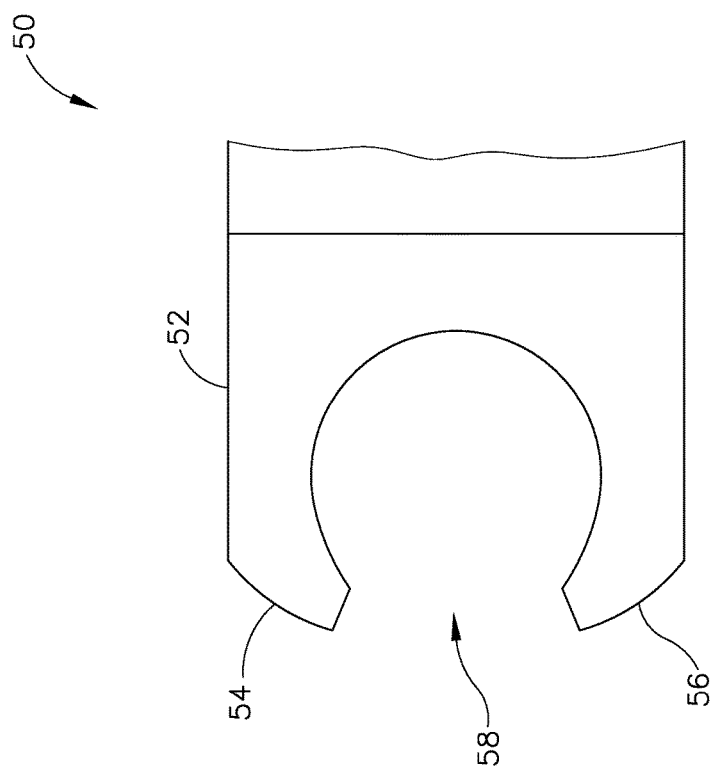
FIG. 2 depicts an enlarged partial elevational view of the end effector of the suturing instrument of FIG. 1.
Figure 3:
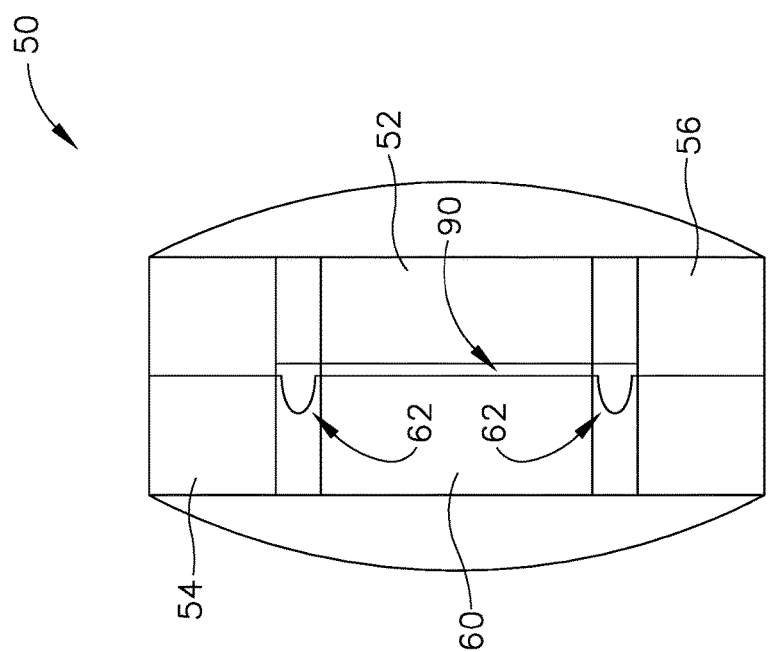
FIG. 3 depicts an end view of the end effector of FIG. 2.
Figure 5:
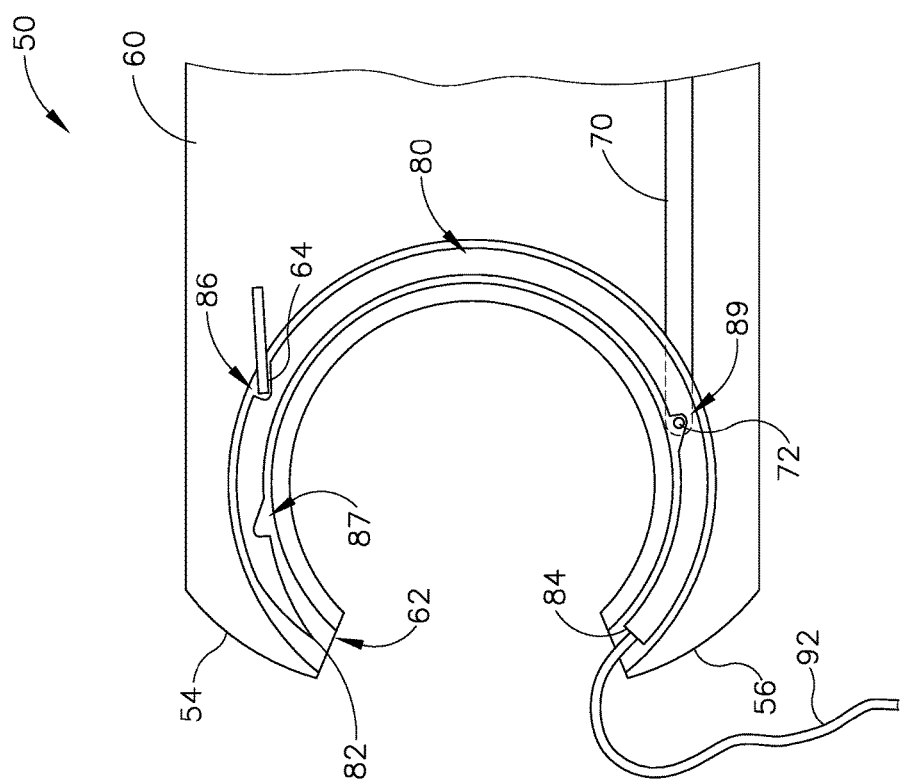
FIG. 5 depicts an enlarged partial elevational view of the needle of FIG. 4 loaded in the end effector of FIG. 2, with a cover of the end effector removed.

FIGS. 2-3 and 5 show end effector (50) of the present example in greater detail. In particular, end effector (50) of the present example comprises a cover (52), a frame base (60), a needle exit arm (54), and a needle entry arm (56). Arms (54, 56) define a gap (58) for receiving tissue, with end effector (50) being operable to drive a needle (80) with suture (92) through the tissue received in gap (58). Frame base (60) defines a curved channel (62) that terminates at the free end of each arm (54, 56) and that is sized to receive a curved needle (80). Cover (52) is movable relative frame base (60) to selectively cover and uncover channel (62) with needle (80) contained therein. By way of example only, cover (52) may slide proximally relative to frame base (60) to selectively uncover channel (62) and needle (80); and distally relative to frame base (60) to selectively cover channel (62) and needle (80). In some other versions, cover (52) may snap on and off of frame base (60), may pivot toward and away from frame base (60), or be movable in some other fashion. It should also be understood that cover (52) may be movable relative to frame base (60) in accordance with at least some of the teachings of U.S. Pat. No. 7,862,572, the disclosure of which is incorporated by reference herein and/or U.S. Pat. No. 7,976,555, the disclosure of which is incorporated by reference herein. As can be seen in FIG. 3, even when cover (52) is positioned over frame base (60) to cover frame base (60) and needle (80), cover (52) and frame base (60) define a gap (90) that is configured to enable suture (92) to travel through gap (90) as needle (80) is being driven along a circular path as described below, thereby preventing suture (92) from getting stuck in channel (62).

Figure 4:
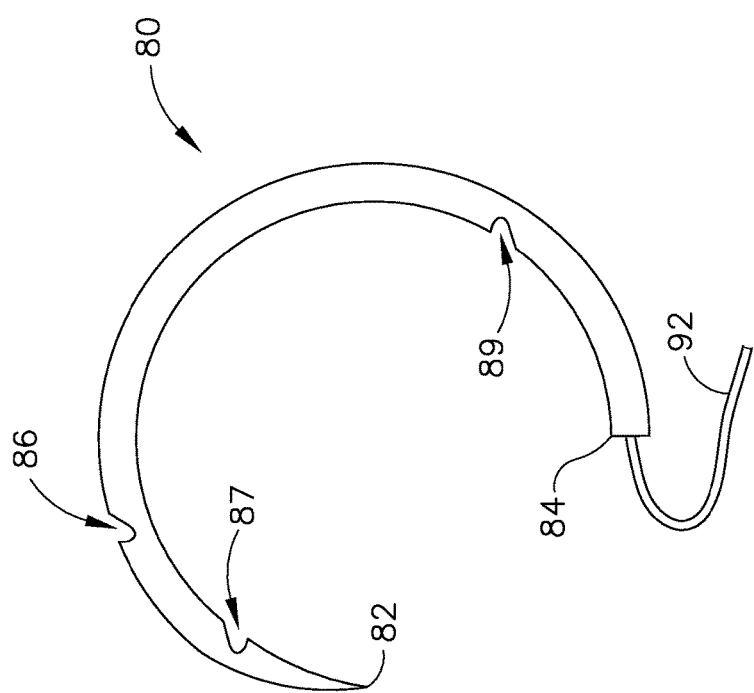
FIG. 4 depicts an elevational view of an exemplary needle suited for use with the suturing instrument of FIG. 1.

As shown in FIG. 4, needle (80) of the present example is curved, forming an incomplete circle. Needle (80) includes a sharp tip (82) and a blunt end (84). In the present example, the body of needle (80) extends along a portion of a circle along approximately 270°, though it should be understood that needle (80) may instead extend through any other suitable angular extent. Sharp tip (82) is configured to pierce tissue repeatedly as needle (80) makes multiple passes through tissue. Suture (92) is integrally secured to the blunt end (84) of needle. Needle (80) is includes an anti-backup notch (86), a needle return notch (87), and a needle drive notch (89). These notches (86, 87, 89) interact with complementary features of end effector (50) as will be described in greater detail below. By way of example only, at least part of needle (80) may be constructed in accordance with at least some of the teachings of U.S. Pub. No. 2012/0123471, entitled "Needle for Laparoscopic Suturing Instrument," published May 17, 2012, now U.S. Pat. No. 9,125,646, issued Sep. 8, 2015, the disclosure of which is incorporated by reference herein, U.S. Pat. No. 7,862,572, the disclosure of which is incorporated by reference herein and/or U.S. Pat. No. 7,976,555, the disclosure of which is incorporated by reference herein.

As shown in FIG. 5, frame base (60) further includes a pawl (64) and a drive arm (70), which has a drive pin (72). Pawl (64) extends distally and has a free end configured to fit in anti-backup notch (86) of needle (80) when needle (80) is in a home position. Pawl (64) is resiliently biased to extend distally but is further configured to deflect laterally when needle (80) is being driven. By way of example only, pawl (64) may comprise a resilient strip of metal that is integrally secured in frame base (60). As another merely illustrative example, pawl (64) may comprise a rigid member that is pivotally secured to frame base (60) and spring-loaded to provide a resilient bias to the position shown in FIG. 5. Various other suitable configurations for pawl (64) will be apparent to those of ordinary skill in the art in view of the teachings herein. Drive pin (72) is configured to fit in needle return notch (87) and in needle drive notch (89). Drive arm (70) is movable to move pin (72) along a circular path, to thereby drive needle (80) along a circular path. Drive arm (70) may move in response to pivoting of trigger (24) toward grip (22), in response to activation of powered motive source (36), or in response to any other suitable type of input. It should be understood that various types of components and assemblies may be employed to actuate drive arm in response to a user input. By way of example only, such components and assemblies may be constructed in accordance with at least some of the teachings of U.S. Pat. No. 7,862,572, the disclosure of which is incorporated by reference herein. Still other suitable components and assemblies that may be employed to drive drive arm (70) will be apparent to those of ordinary skill in the art in view of the teachings herein.

Figure 6A:
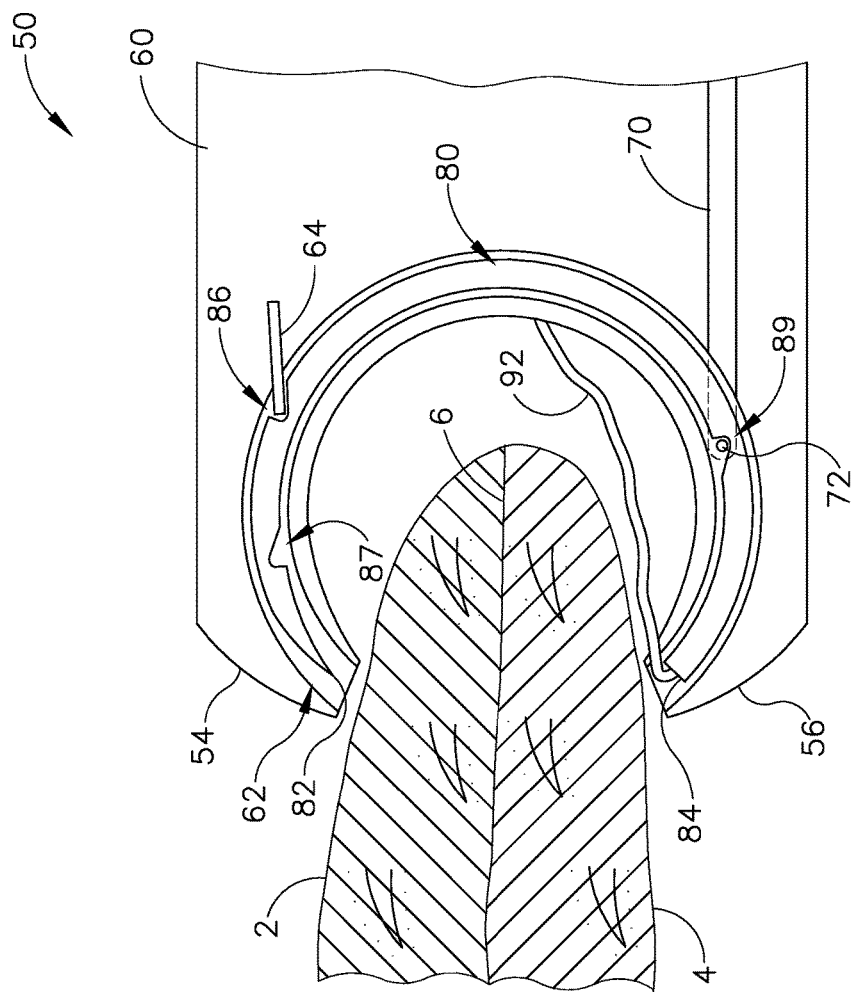
FIG. 6A depicts an enlarged partial elevational view of the loaded end effector of FIG. 5, with the end effector positioned about tissue.
Figure 6B:
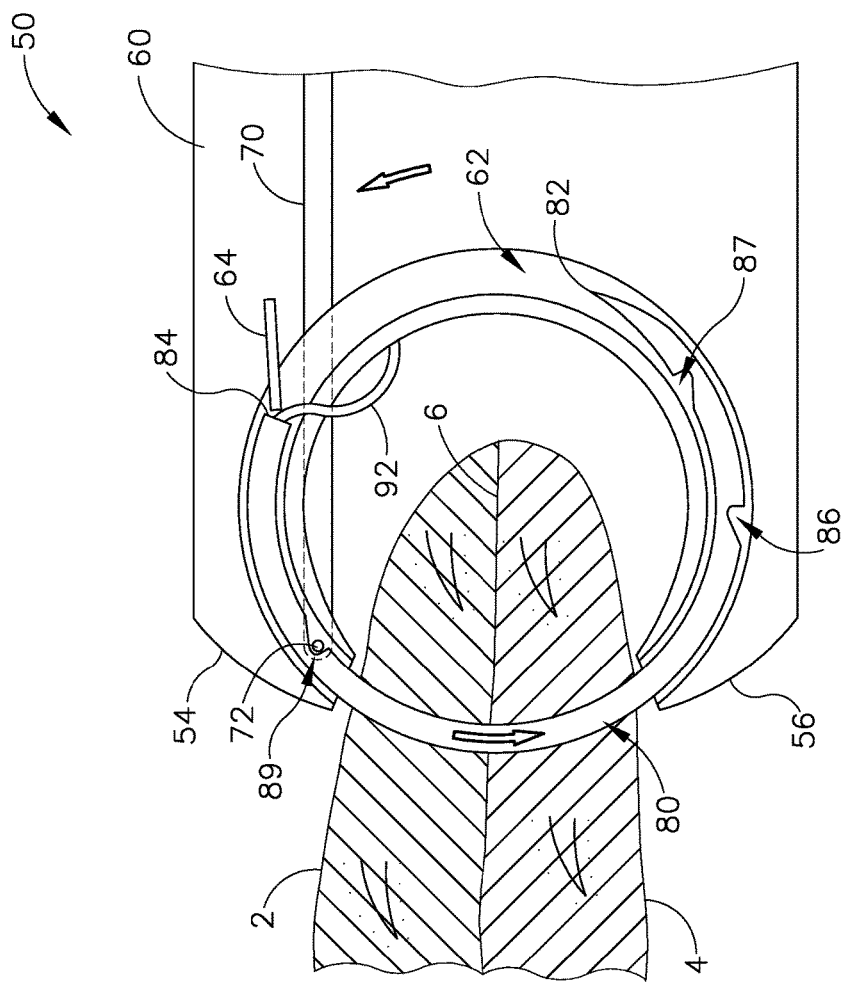
FIG. 6B depicts an enlarged partial elevational view of the loaded end effector of FIG. 5, with the end effector driving the needle through the tissue.

FIGS. 6A-6E show exemplary stages of use of end effector (50) to securely close an incision (6) that splits two layers (2, 4) of tissue. In some uses, end effector (50) is used to simply close an incision (6) that was formed by cutting a single planar layer of tissue with a cutting instrument in a single anatomical structure, with two apposed layers (2, 4) being formed by folding and pinching together the single layer in order to engage end effector (50). In some other uses, end effector (50) is used to suture a layer (2) of tissue of one anatomical structure to a layer (4) of tissue of another anatomical structure. Other suitable contexts for using end effector (50) will be apparent to those of ordinary skill in the art in view of the teachings herein. As shown in FIG. 6A, layers (2, 4) are positioned in gap (58) between arms (54, 56). By way of example only, layers (2, 4) may be manipulated using a set of conventional tissue graspers and/or any other suitable instrumentation to position layers (2, 4) in gap (58). With layers (2, 4) suitably positioned, drive arm (70) is actuated as shown in FIG. 6B to drive needle (80) along a circular path (counterclockwise in the views shown in FIGS. 6A-6E). The orbital motion of arm (70) is transferred to needle (80) via pin (72) in needle drive notch (89). This orbital motion drives needle (80) approximately 180° along a circular path. During this travel, tip (82) pierces both layers (2, 4) of tissue, such that needle (80) is disposed in both layers (2, 4) of tissue.

Figure 6C:
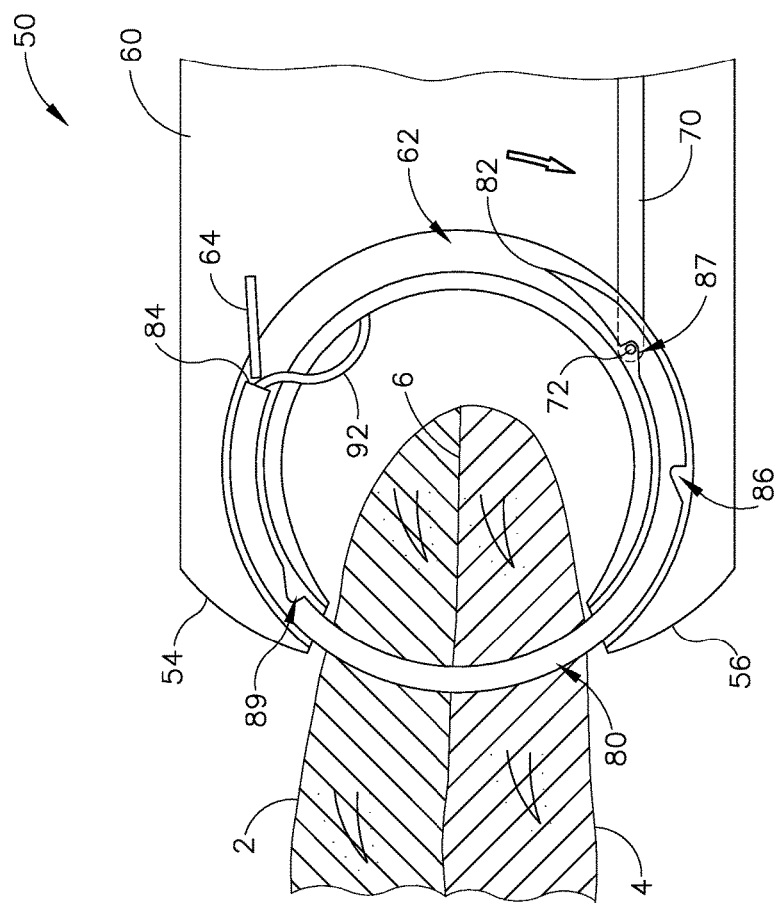
FIG. 6C depicts an enlarged partial elevational view of the loaded end effector of FIG. 5, with the end effector resetting a needle driver.
Figure 6D:
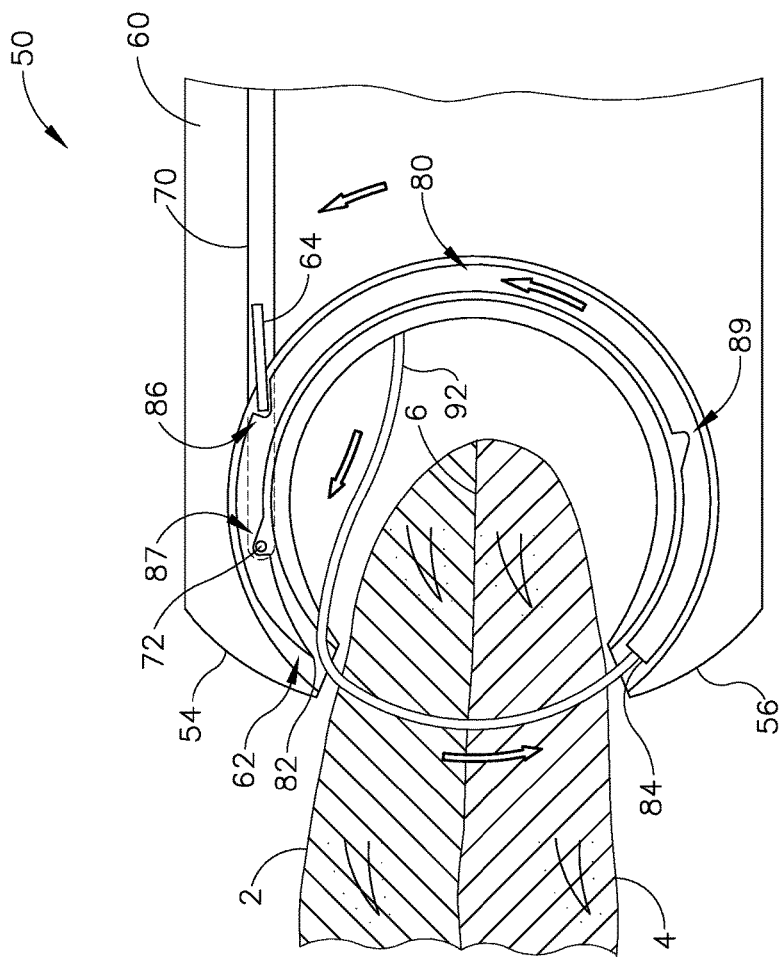
FIG. 6D depicts an enlarged partial elevational view of the loaded end effector of FIG. 5, with the end effector completing a pass of the needle through the tissue, thereby drawing suture through the tissue.

As shown in FIG. 6B, suture (92) has been pulled due to needle (80) being driven along the circular path through channel (62). However, suture (92) does not completely follow needle (80) along the path through channel (62). Instead, suture (92) travels through (90) gap. This allows suture (92) to avoid getting repeatedly wrapped through channel (62) as needle (80) is repeatedly driven through channel (62). As also shown in FIG. 6B, the free end of pawl (64) is positioned behind blunt end (84) of needle (80) at this stage. This prevents needle (80) from traveling in reverse (clockwise in the views shown in FIGS. 6A-6E) as drive arm (70) is returned to the home position as shown in FIG. 6C. When drive arm (70) is driven from the actuated position (FIG. 6B) back to the home position (FIG. 6C), pin (72) pivots away from needle (80) and out of engagement with needle drive notch (89). By way of example only, pin (72) may selectively disengage notch (89) in accordance with at least some of the teachings of U.S. Pat. No. 7,862,572, the disclosure of which is incorporated by reference herein. Still other suitable ways in which pin (72) may selectively disengage notch (89) for return of arm (70) to the home position will be apparent to those of ordinary skill in the art in view of the teachings herein.

With arm (70) to the home position as shown in FIG. 6C, pin (72) is disposed in needle return notch (87). This enables arm (70) to continue driving needle (80) along the circular path, to the position shown in FIG. 6D. In this position, needle (80) has returned to the same home position previously shown in FIG. 6A, such that needle (80) has been completely pulled through both layers (2, 4) of tissue. Needle (80) has thus traveled through a full 360° circular orbital path at this stage, and has thereby completed a full drive stroke. This further results in needle (80) pulling suture (92) through both layers (2, 4) of tissue. Pawl (64) is once again disposed in anti-backup notch (86), again preventing reversal of needle (80). Arm (70) is then again moved back to the home position, with pin (72) disengaging needle return notch (87) in the same manner as the disengagement of pin (72) from needle drive notch (89) as described above.

Figure 6E:
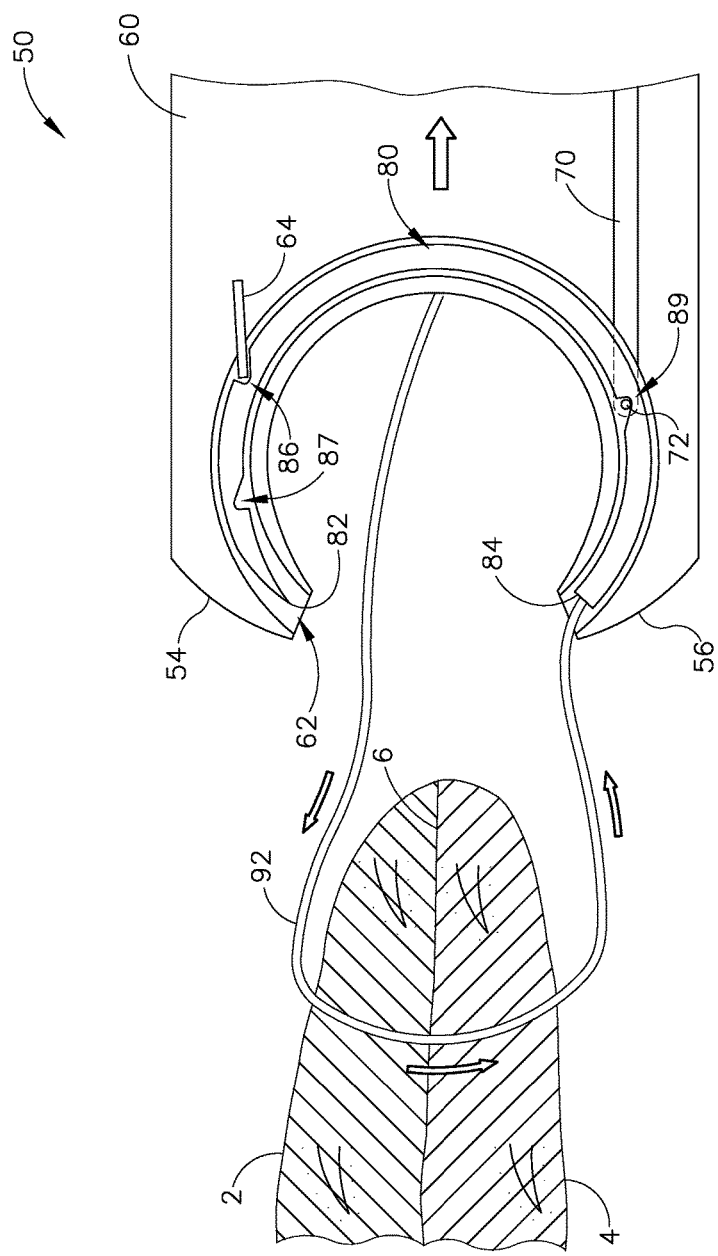
FIG. 6E depicts an enlarged partial elevational view of the loaded end effector of FIG. 5, with the end effector being pulled away from the tissue to pull additional suture through the tissue.
Figure 7:
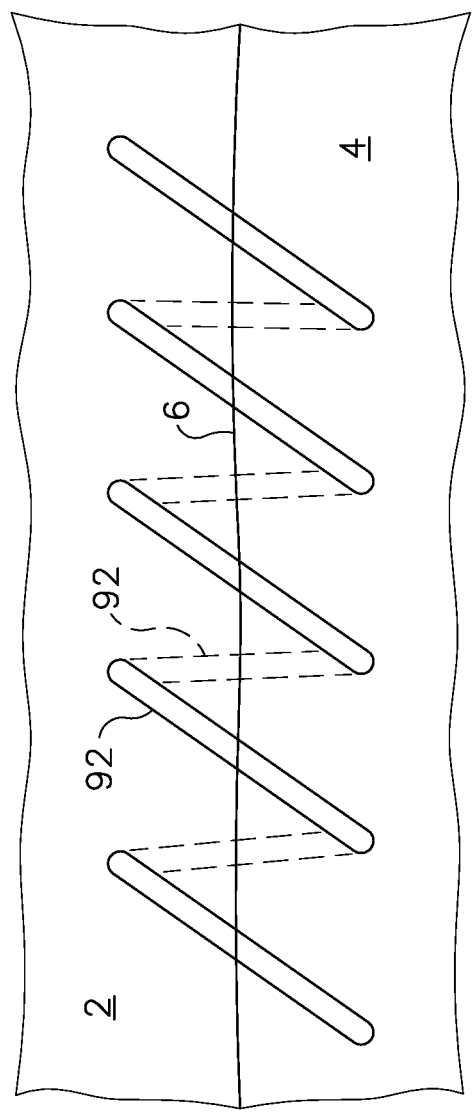
FIG. 7 depicts a top plan view of tissue sutured using the instrument of FIG. 1.
Figure 8:
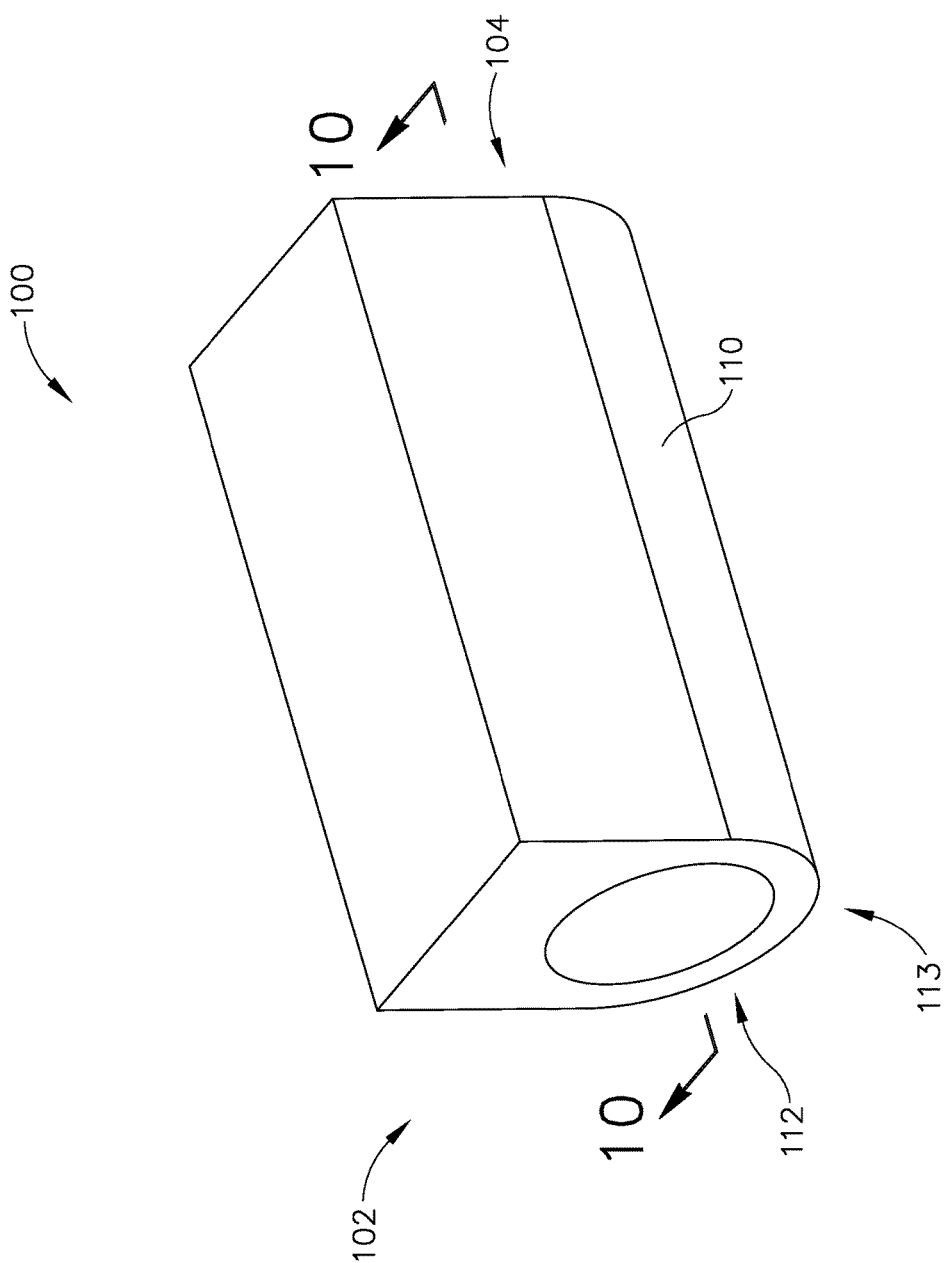
FIG. 8 depicts a perspective view of an exemplary needle loader suitable for use with the instrument of FIG. 1.

With arm (70) being returned to the home position, the entire end effector (50) is then pulled away from layers (2, 4) of tissue to draw suture (92) through layers (2, 4) of tissue as shown in FIG. 6E. To the extent that this creates tension on suture (92) that might urge needle (80) to back out through channel (62), engagement between pawl (64) and anti-backup notch (86) prevents such backing out of needle (80). After pulling additional length of suture (92) through layers (2, 4) of tissue as shown in FIG. 6E, end effector (50) may be moved to another position along incision (6), with layers (2, 4) being repositioned in gap (58), such that the process shown in FIGS. 6A-6E may be repeated any number of times as desired to create a series of stitches along incision (6). The resulting stitches may appear similar to what is shown in FIG. 7. As shown, the portion of suture (92) disposed within layers (2, 4) of tissue is oriented generally transversely to the line defined by incision (60); while the portion of suture (92) that is external to layers (2, 4) of tissue is oriented obliquely relative to the line defined by incision (60). Of course, suture (92) may instead have any other types of configurations after being passed through layers (2, 4) of tissue to form a series of stitches. Other suitable ways in which instrument (10) may be used will be apparent to those of ordinary skill in the art in view of the teachings herein.

II. Exemplary Needle Loaders

In some instances, it may be necessary for an operator to load a needle (80) in end effector (50). This may be necessary before a suturing procedure begins. This may also be necessary in the middle of a suturing procedure, such that operator may discard a used needle (80) from end effector (50) and replace it with a new needle (80). It may be desirable to make this process fast and easy; and to avoid risks of an operator inadvertently contacting sharp tip (82) while loading needle (80) in end effector. Accordingly, it may be desirable to provide a needle loading cartridge that may receive end effector (50) for substantially automated loading of a needle (80). Various examples of needle loading cartridges will be described in greater detail below; while other examples will be apparent to those of ordinary skill in the art in view of the teachings herein.

A. First Exemplary Automated Needle Loader

FIGS. 8-10D show an exemplary needle loader (100) that may be used to load a needle (80) in end effector (50). Needle loader (100) comprises a body (110), a lever (120), and needle (80). Body (110) presents a channel (112) and an engagement feature (114). Channel (112) is configured to receive end effector (50) of instrument (10). As best seen in FIG. 9, the width of engagement feature (114) is less than the width of channel (112) at the point where engagement feature (114) protrudes into channel (112), such that a portion of channel (112) is on either side of engagement feature (114). As seen in FIG. 10A, body (110) further comprises a cavity (116) located toward a distal portion (104) of body (110). Lever (120) is pivotably disposed within cavity (116) of body (110). Lever (120) comprises a first arm (121) and a second arm (123) and pivots about a pivot member (122). Cavity (116) is configured to allow lever (120) to pivot about pivot member (122) while maintaining the general location of pivot member (122). A first opening (126) and a second opening (124) connect cavity (116) with a distal portion (115) of channel (112). A drive member (128) extends proximally from lever (120) through opening (126) and into distal portion (115) of channel (112). Needle (80) is releasably secured within a second opening (124) such that a portion of needle (80) extends into cavity (116) as shown in FIG. 10A. By way of example only, a magnet, tabs, crush ribs, and/or any other suitable feature(s) may be used to releasably secure needle (80) in opening (124).

Figure 10A:
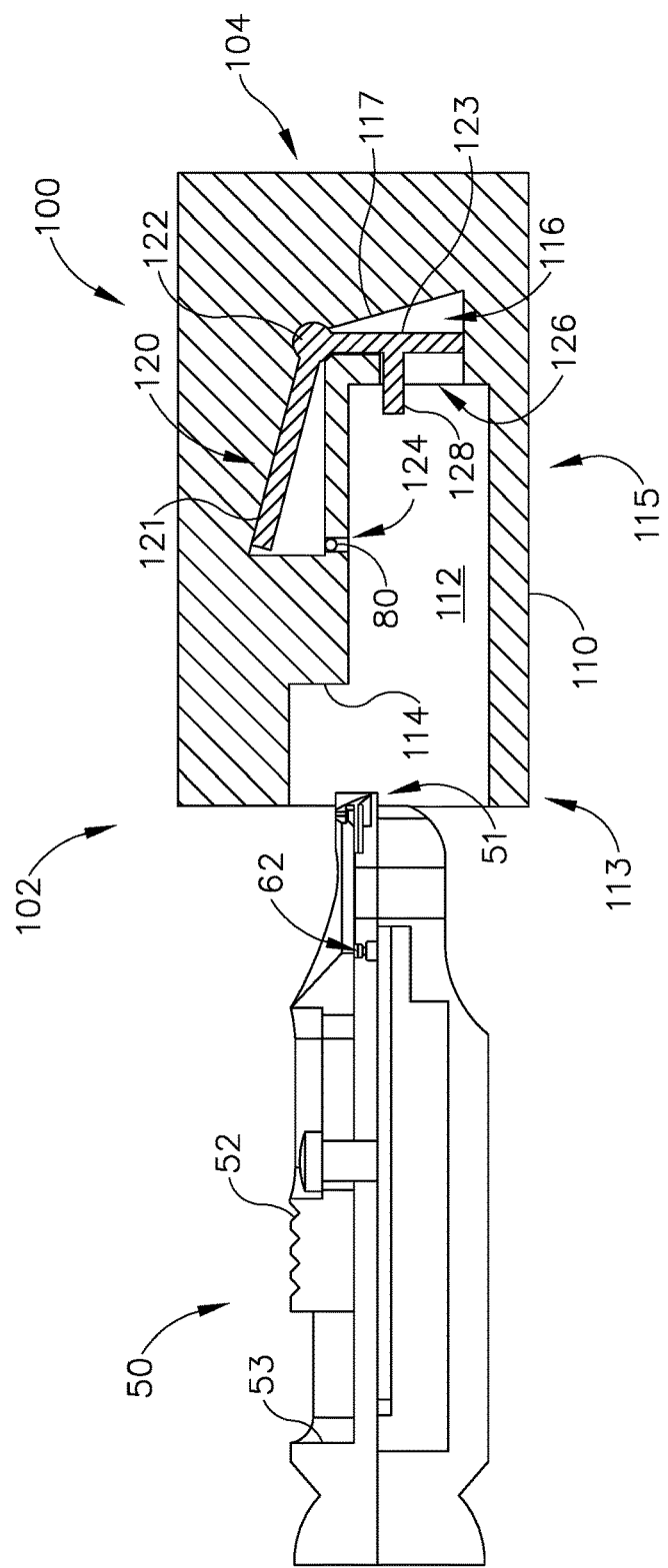
FIG. 10A depicts a side cross sectional view, taken along line 10-10 of FIG. 8, of the suturing instrument of FIG. 1 being inserted into the needle loader of FIG. 8.
Figure 10B:
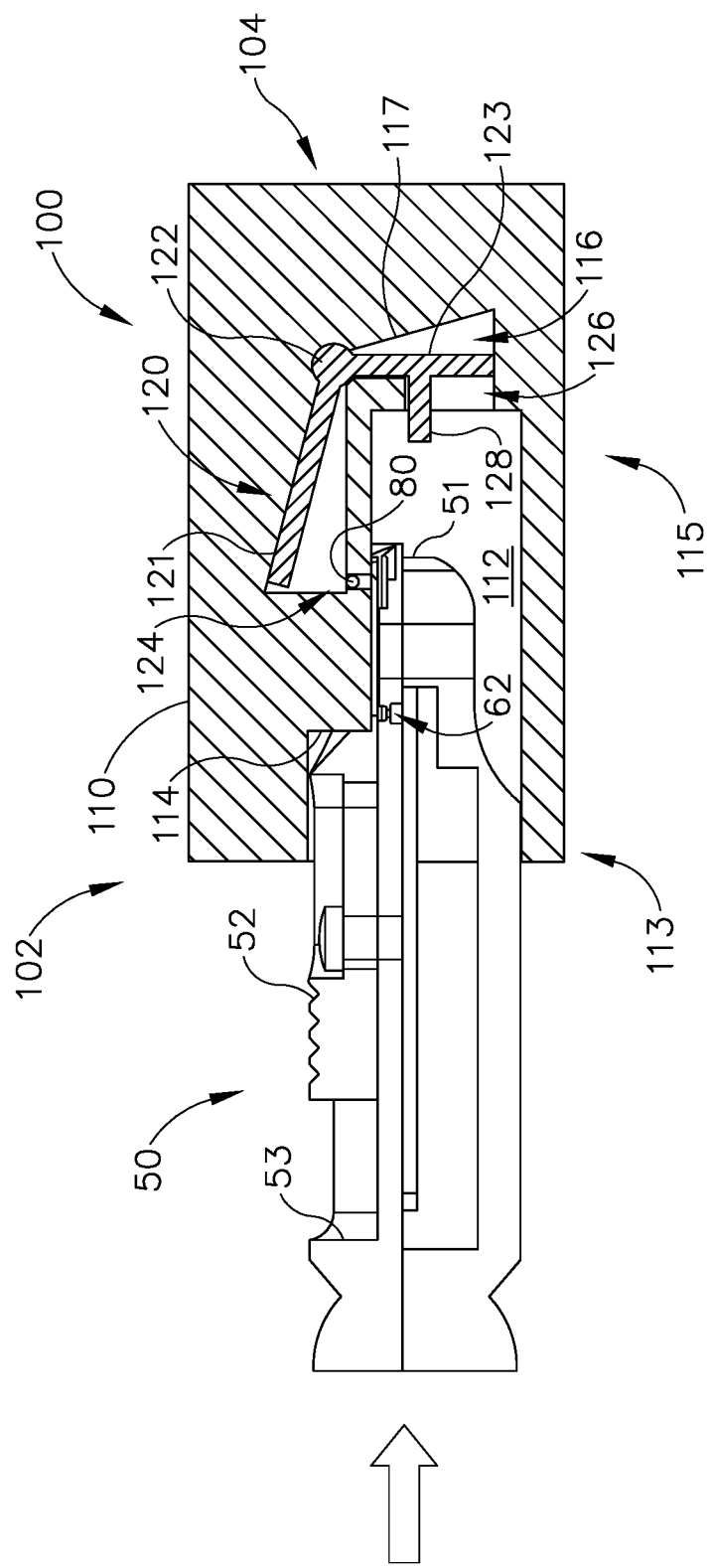
FIG. 10B depicts a side cross sectional view, taken along line 10-10 of FIG. 8, of an engagement feature of the needle loader of FIG. 8 engaging a cover of the suturing instrument of FIG. 1.
Figure 10C:
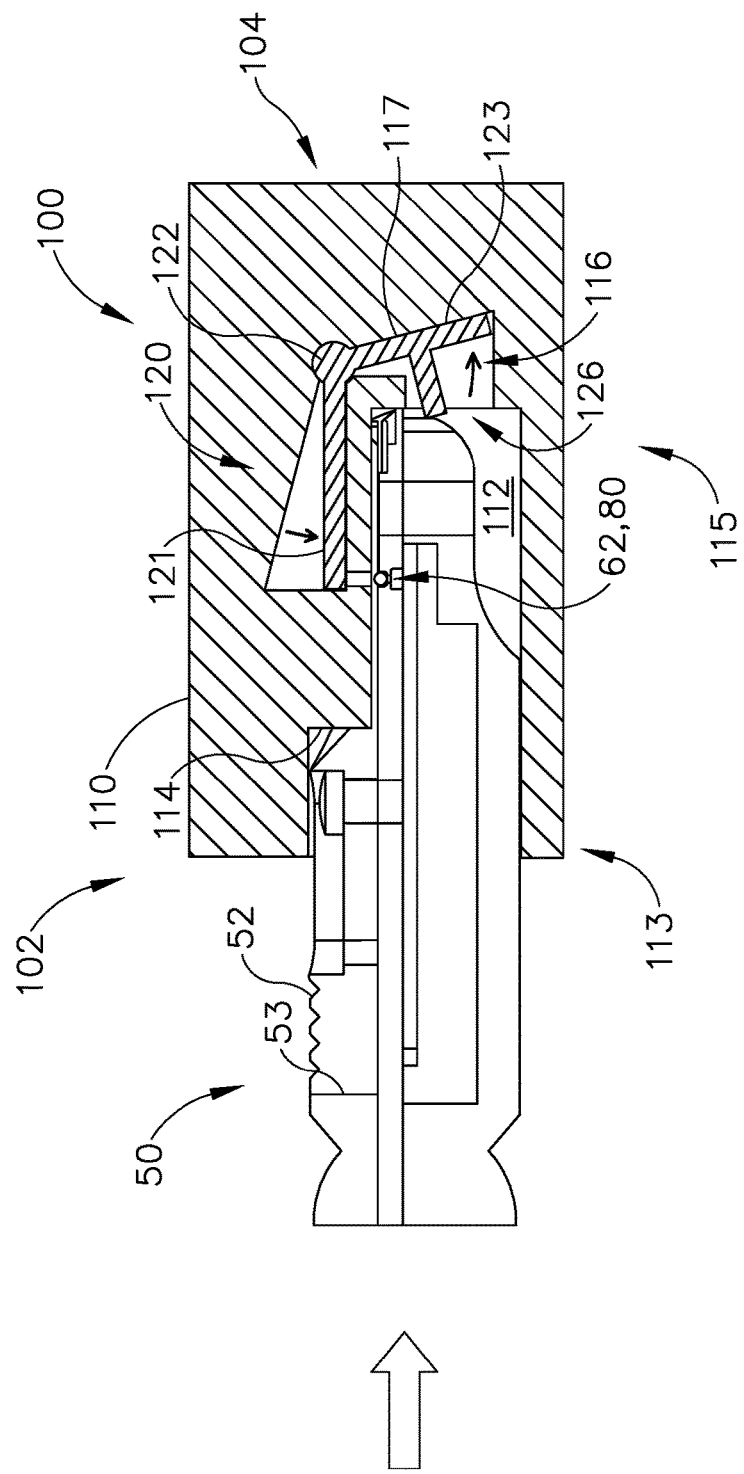
FIG. 10C depicts a side cross sectional view, taken along line 10-10 of FIG. 8, of the suturing instrument of FIG. 1 engaging a lever of the needle loader of FIG. 8 and receiving a needle.

In an exemplary use, needle loader (100) is used to insert needle (80) into curved channel (62) of end effector (50). As shown in FIG. 10A, end effector (50) of instrument (10) is inserted into a proximal portion (113) of channel (112). End effector (50) is oriented such that cover (52) of end effector (50) is up. As shown in FIG. 10B, end effector (50) is inserted further distally into channel (112) along a longitudinal axis defined by channel (112). During the process of inserting end effector (50) into channel (112), engagement feature (114) contacts cover (52) and begins to drive cover (52) in a proximal direction. As shown in FIG. 10C, end effector (50) is further distally inserted into channel (112) along the longitudinal axis defined by channel (112) until a distal end (51) of end effector (50) contacts drive member (128) of lever (120) and drives second arm (123) into a distal wall (117) of cavity (116) such that end effector (50) cannot be further inserted into channel (112). It should be understood, that at this point, engagement feature (114) will have driven cover (52) in a proximal direction so that curved channel (62) is completely exposed.

Figure 10D:
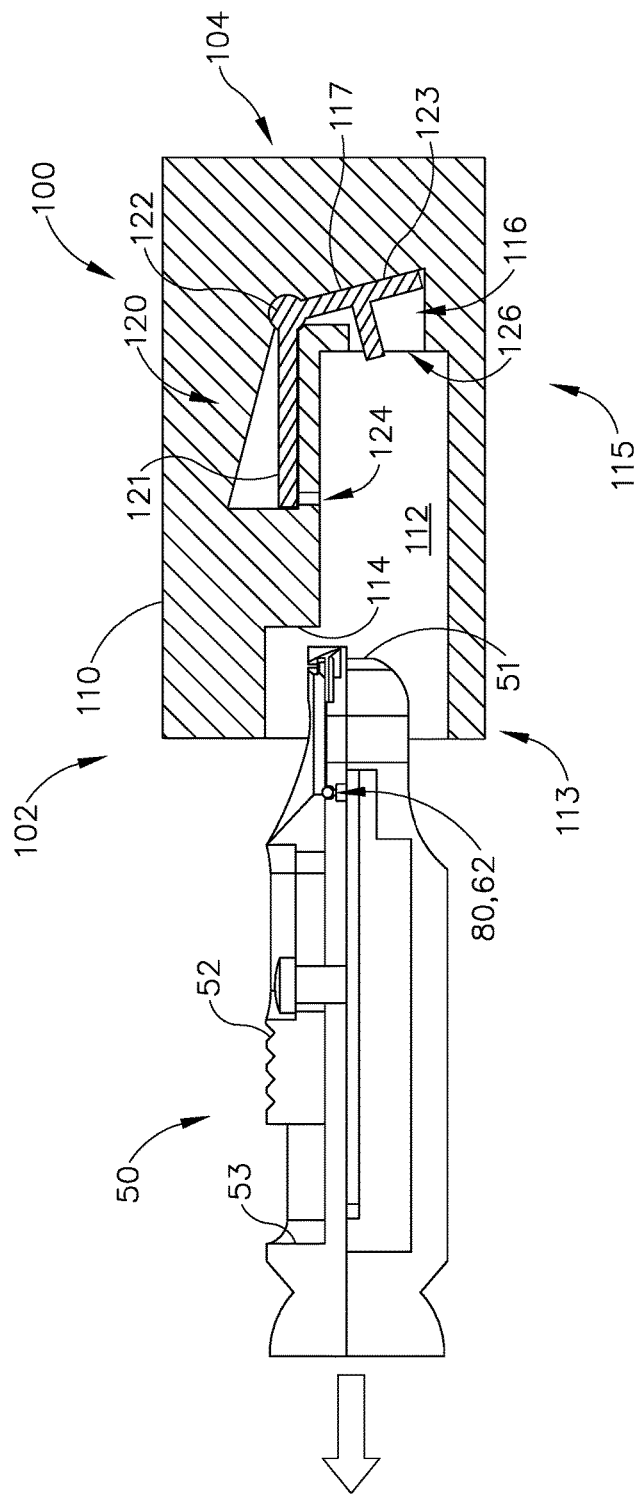
FIG. 10D depicts a side cross sectional view, taken along line 10-10 of FIG. 8, of the suturing instrument of FIG. 1 being removed from the needle loader of FIG. 8.
Figure 11:
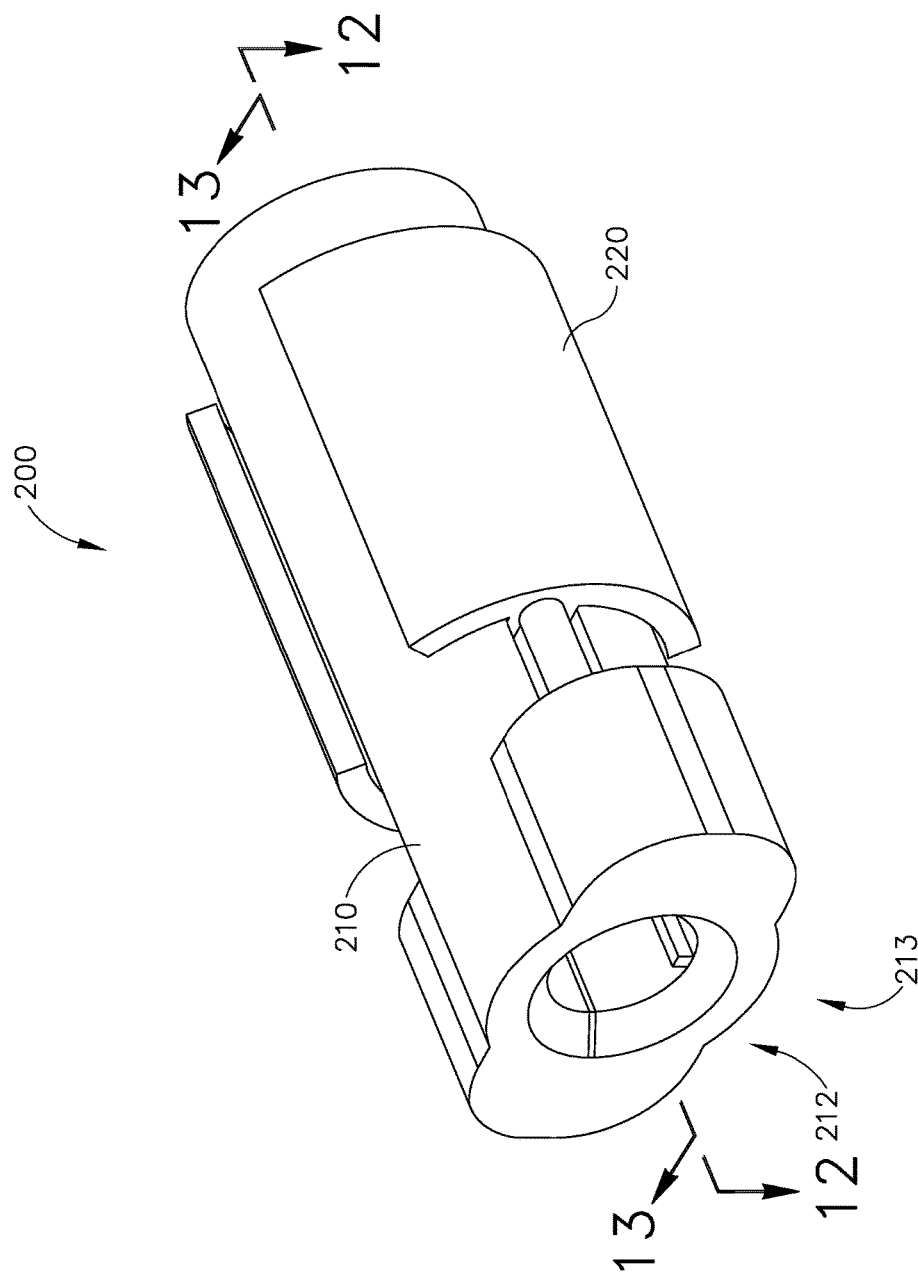
FIG. 11 depicts a perspective view of an exemplary alternative needle loader suitable for use with the instrument of FIG. 1.

The distal movement of second arm (123) caused by insertion of end effector (50) into channel (112), will cause lever (120) to pivot about pivot member (122) and first arm (121) to move in a downward direction. Downward movement of first arm (121) will cause first arm (121) to contact needle (80). The force of this contact drives needle (80) out of opening (124) into curved channel (62). In some versions, a downwardly projecting feature (not shown) of first arm (121) contacts needle (80) and assists in driving needle (80) out through opening (124). Such a downwardly projecting feature may remain disposed in opening (124) after lever (120) has pivoted to the position shown in FIG. 10C. As shown in FIG. 10D, as end effector (50) is removed from channel (112), cover (52) returns to its original position under the resilient bias of a spring in end effector (50), because cover (52) is no longer being driven by engagement feature (114).

Once end effector (50) is completely removed from needle loader (100), instrument (10) is ready for use. It should be noted that needle loader (100) may further comprise suturing thread within body (110), such that the suturing thread is spooled about an internal or external portion of body (110). Such suturing thread may be already secured to needle (80), such that the operator will pull suturing thread from body (110) as the operator pulls the loaded end effector (50) away from body (110). However, body (110) need not comprise suturing thread. By way of example only, suturing thread may be provided as a separate component of needle loader (100).

B. Second Exemplary Automated Needle Loader

Figure 12:
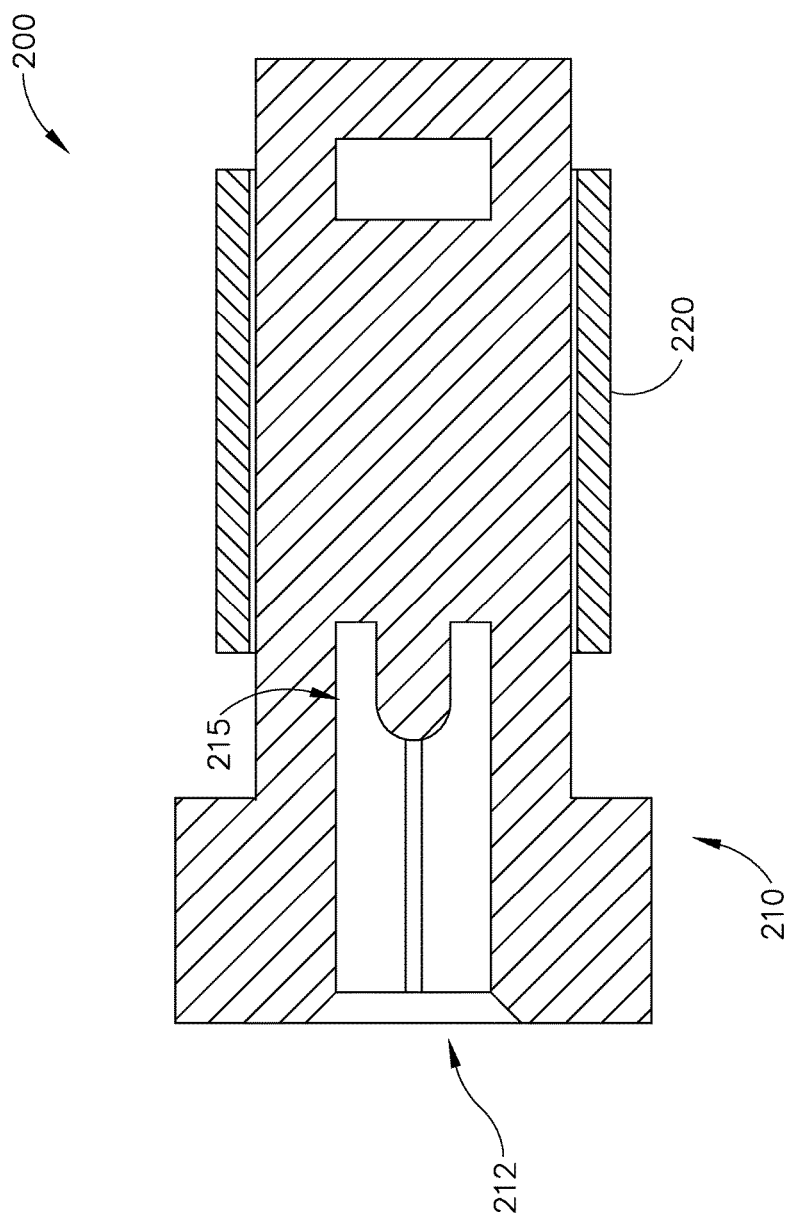
FIG. 12 depicts a cross sectional top view of the needle loader of FIG. 11, taken along line 12-12 of FIG. 11.

FIGS. 11-13D show an exemplary alternative needle loader (200) that may be used to load a needle (80) in end effector (50). Needle loader (200) of this example comprises a body (210), a sliding member (220), a drive member (230), and needle (80). Body (210) presents a first channel (212) and a second channel (216). First channel (212) is configured to receive end effector (50) of instrument (10). As seen in FIG. 12, a distal portion (215) of first channel (212) is forked such that distal portion (215) of first channel (212) will receive needle exit arm (54) and needle entry arm (56). Second channel (216) is configured to slidably receive sliding member (220). As seen in FIG. 13A, body (210) presents a camming ramp (219) located at a proximal end of second channel (216) along the top surface of second channel (216). Sliding member (220) comprises an engagement feature (214) and an opening (224). Needle (80) is disposed within opening (224) and rests upon the bottom surface second channel (216). Drive member (230) is slidably disposed within opening (224) and rests upon needle (80).

Figure 13A:
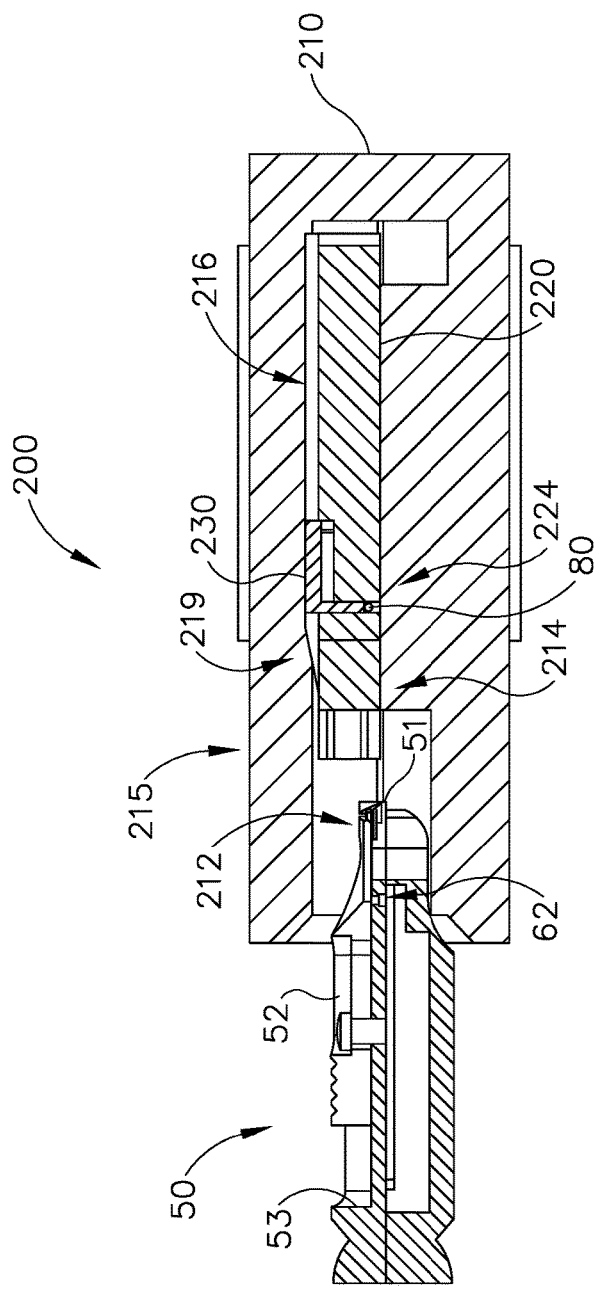
FIG. 13A depicts a side cross sectional view, taken along line 13-13 of FIG. 11, of the suturing instrument of FIG. 1 being inserted into the needle loader of FIG. 11.
Figure 13B:
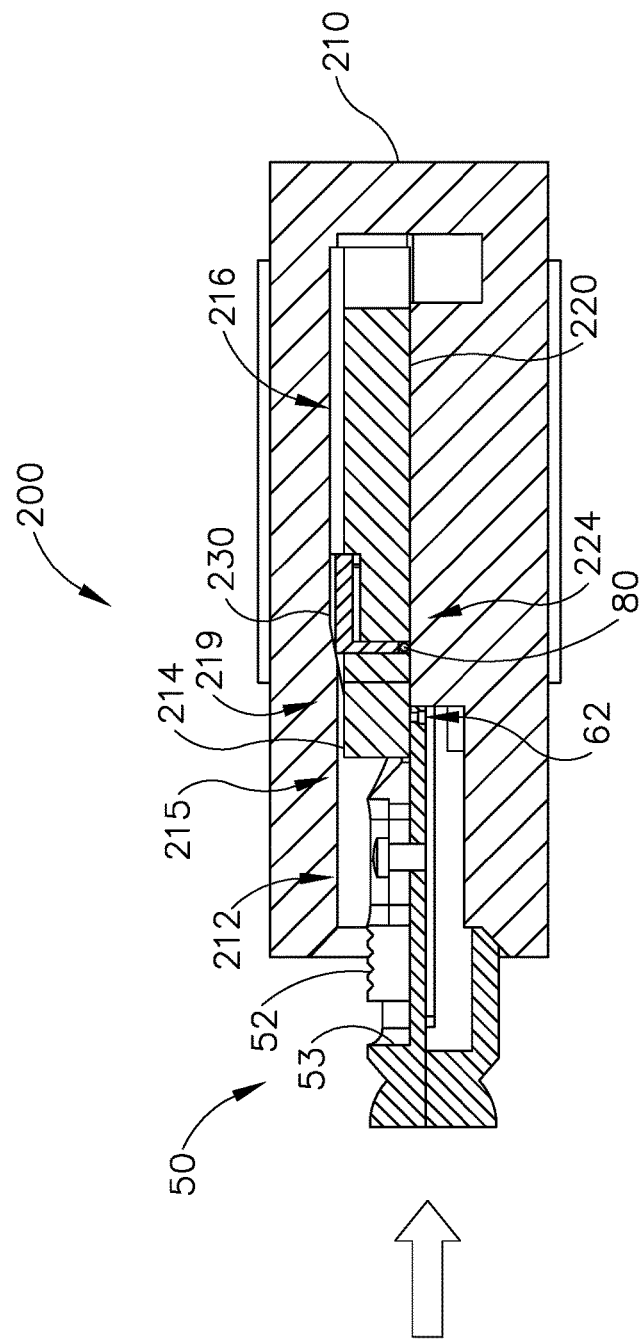
FIG. 13B depicts a side cross sectional view, taken along line 13-13 of FIG. 11, of an engagement feature of the needle loader of FIG. 11 engaging a cover of the suturing instrument of FIG. 1.
Figure 13C:
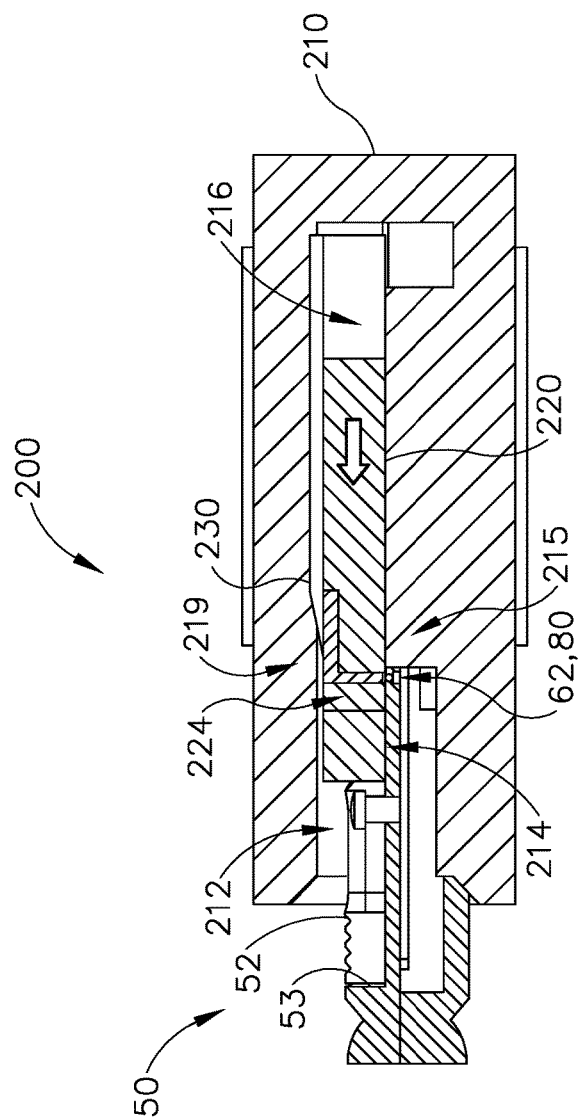
FIG. 13C depicts a side cross sectional view, taken along line 13-13 of FIG. 11, of the suturing instrument of FIG. 1 receiving a needle from the needle loader of FIG. 11.

In an exemplary use, needle loader (200) is used to insert needle (80) into curved channel (62) of end effector (50). As shown in FIG. 13A, end effector (50) of instrument (10) is inserted into a proximal portion (213) of first channel (212). End effector (50) is oriented such that cover (52) of end effector (50) is up. As shown in FIG. 13B, end effector (50) is further distally inserted into first channel (212) along a longitudinal axis defined by first channel (212) until a distal end (51) of end effector (50) contacts a distal wall (217) of first channel (212) such that end effector (50) cannot be further inserted into first channel (212). Sliding member (220) is then moved in a proximal direction parallel to the longitudinal axis defined by first channel (212). For instance, the operator may grasp needle loader (200) by sliding member (220) and pull needle loader (200) proximally relative to end effector (50) while grasping sliding member (220). Once end effector (50) contacts distal wall (217), body (210) will come to a stop while sliding member (220) continues to move proximally as the operator continues to pull proximally. During the process of moving sliding member (220) proximally, engagement feature (214) contacts cover (52) and begins to drive cover (52) in a proximal direction. Also during the process of moving sliding member (220), drive member (230) contacts ramp (219). Ramp (219) is angled such that the proximal movement of sliding member (220) parallel to the longitudinal axis defined by first channel (212) exerts a downward force upon drive member (230) and consequently needle (80). This downward force is initially counteracted by a force from the bottom surface of second channel (216).

Figure 13D:
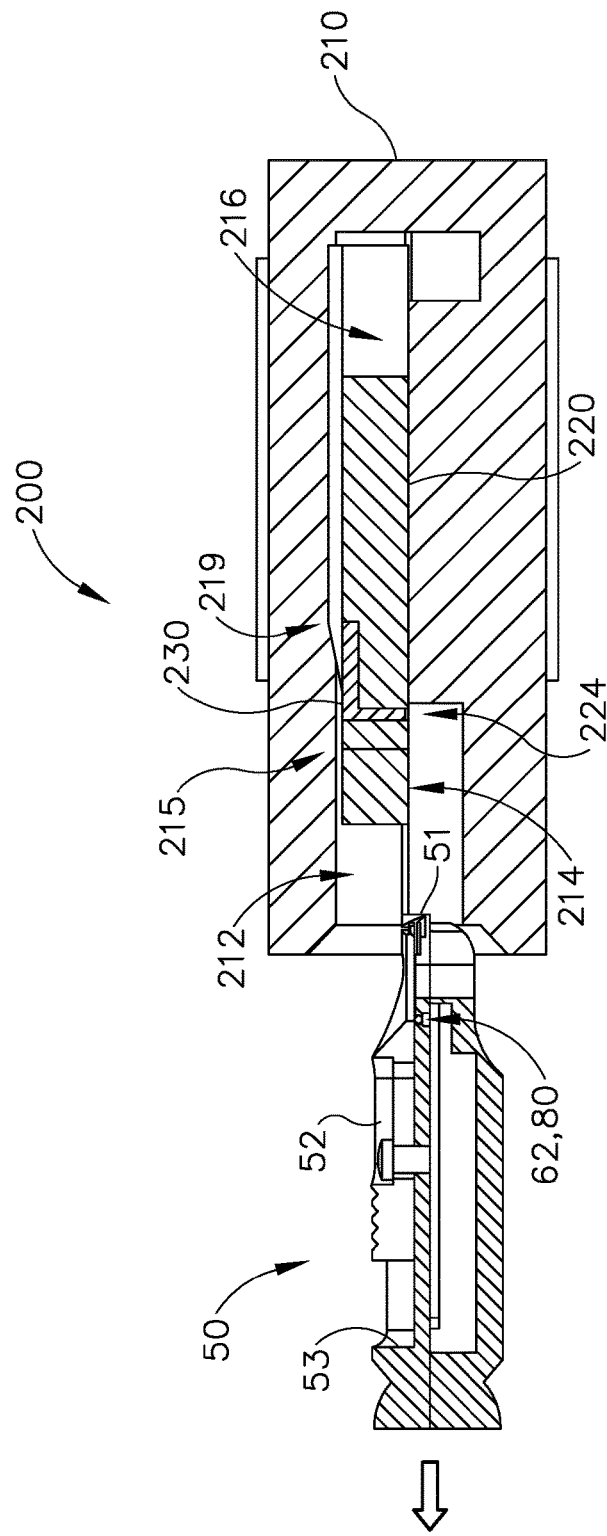
FIG. 13D depicts a side cross sectional view, taken along line 13-13 of FIG. 11, of the suturing instrument of FIG. 1 being removed from the needle loader of FIG. 11.

Once sliding member (220) contacts body (210), such that sliding member (220) cannot be moved further proximally, needle (80) will no longer be supported by the bottom surface of second channel (216) and needle (80) will be driven downwardly by drive member (230) into curved channel (62). It should be understood, that at this point, engagement feature (214) will have driven cover (52) in a proximal direction so that curved channel (62) is completely exposed. As shown in FIG. 13D, as end effector (50) is removed from first channel (212), cover (52) returns to its original position under the resilient bias of a spring in end effector (50), because cover (52) is no longer being driven by engagement feature (214).

Once end effector (50) is completely removed from needle loader (200), instrument (10) is ready for use. It should be noted that needle loader (200) may further comprise suturing thread within body (210), such that the suturing thread is spooled about an internal or external portion of body (210). Such suturing thread may be already secured to needle (80), such that the operator will pull suturing thread from body (210) as the operator pulls the loaded end effector (50) away from body (210). However, body (210) need not comprise suturing thread. By way of example only, suturing thread may be provided as a separate component of needle loader (200).

C. Third Exemplary Automated Needle Loader

Figure 15:
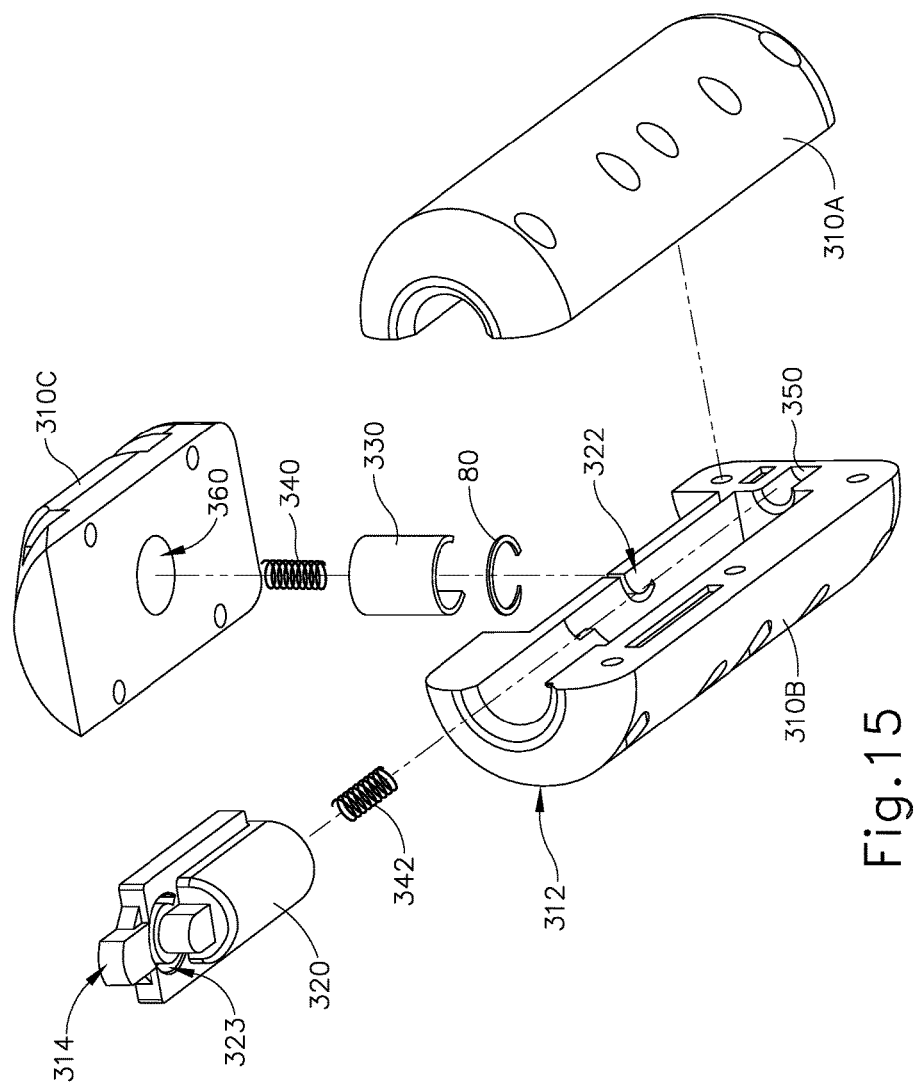
FIG. 15 depicts an exploded perspective view of the needle loader of FIG. 14.

FIGS. 14-16D show another exemplary alternative needle loader (300) that may be used to load a needle (80) in end effector (50). Needle loader (300) of this example comprises a body (310), a sliding member (320), a drive member (330), a first spring (340), a second spring (342), and needle (80). Body (310) comprises a first portion (310A), a second portion (310B), and a third portion (310C). First portion (310A) and second portion (310B) of body (310) together define a first channel (312) and a first needle-shaped opening (322), which will be discussed in more detail below. First channel (312) is configured to receive end effector (50) of instrument (10). As seen in FIG. 15, a distal portion (315) of first channel (312) comprises a proximally opening first recess (350). Sliding member (320) is slidably disposed within first channel (312). Sliding member (320) comprises a distally opening second recess (352) that aligns with first recess (350). First spring (342) is partially disposed within first recess (350) and second recess (352) such that an end of first spring (342) is within first recess (350) and another end of first spring (342) is within second recess (352). First spring (342) biases sliding member (320) proximally in channel (312). Sliding member (320) further comprises an engagement feature (314) and a second needle-shaped opening (323) which will be discussed in more detail below.

Figure 16A:
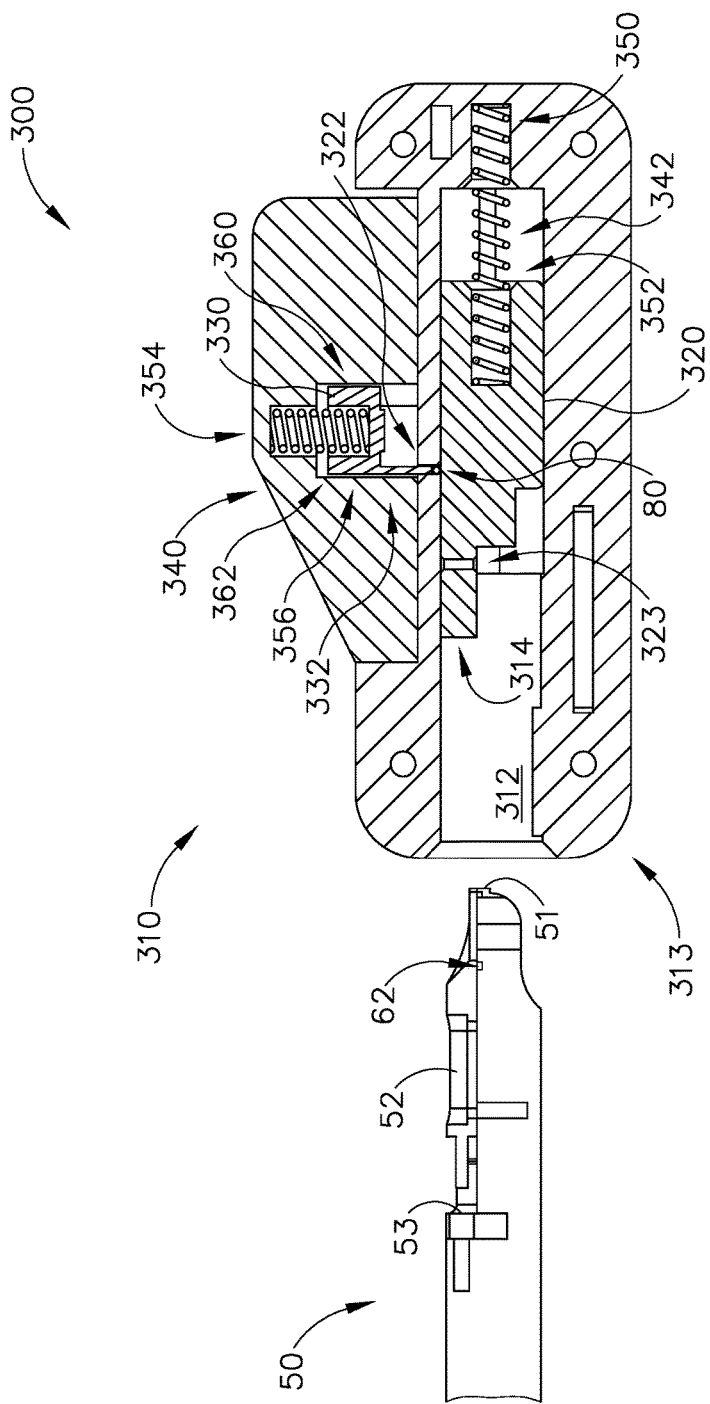
FIG. 16A depicts a side cross sectional view, taken along line 16-16 of FIG. 14, of the suturing instrument of FIG. 1 being inserted into the needle loader of FIG. 14.

Third portion (310C) of body (310) is coupled to the top surfaces of first portion (310A) and second portion (310B). Third portion (310C) comprises a second channel (360). As seen in FIG. 16A, an upper portion (362) of second channel (360) comprises a downwardly opening third recess (354). Drive member (330) is slidably disposed within second channel (360). Sliding member (330) comprises an upwardly opening fourth recess (356) that aligns with third recess (354). Second spring (340) is partially disposed within third recess (354) and fourth recess (356) such that an end of second spring (340) is within third recess (354) and another end of second spring (340) is within fourth recess (356). Second spring (340) biases drive member (330) downwardly in channel (360). Drive member (330) comprises a needle-shaped protrusion (332) that aligns with first needle-shaped opening (322). Needle (80) is disposed within first needle-shaped opening (322) and needle-shaped protrusion (332) of drive member (330) rests upon needle (80). Second spring (340) exerts a downward force upon drive member (330) and consequently needle (80). This downward force is initially counteracted by a force from the top surface of sliding member (320).

Figure 16B:
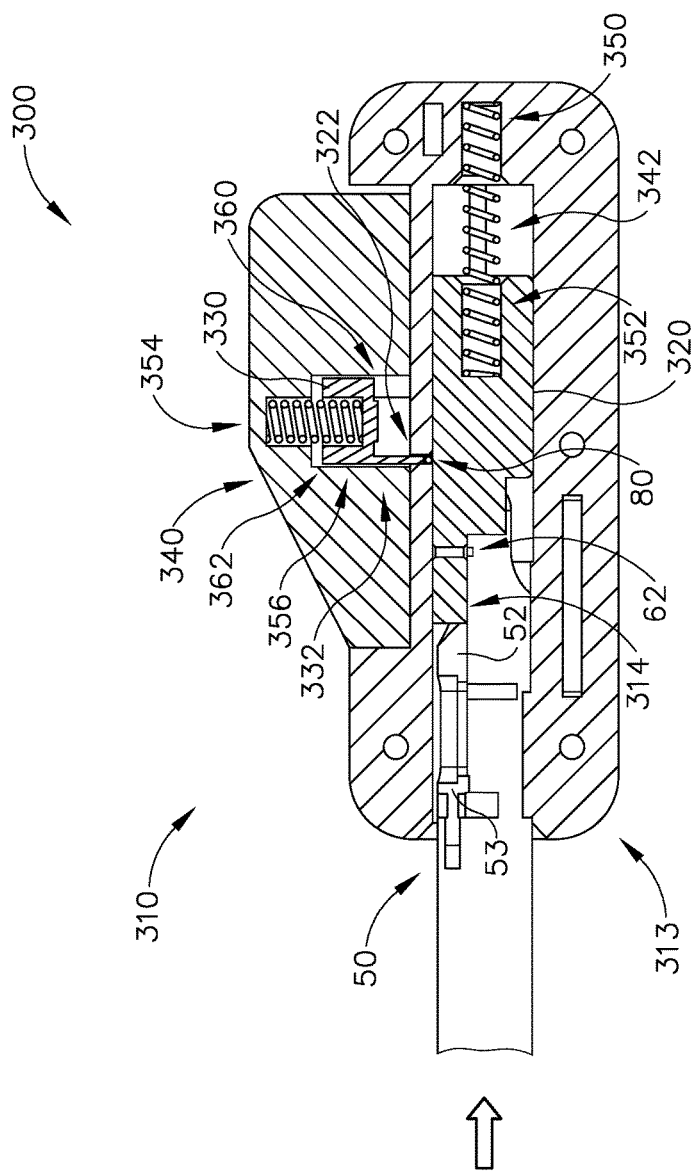
FIG. 16B depicts a side cross sectional view, taken along line 16-16 of FIG. 14, of an engagement feature of the needle loader of FIG. 14 engaging a cover of the suturing instrument of FIG. 1.

In an exemplary use, needle loader (300) is used to insert needle (80) into curved channel (62) of end effector (50). As shown in FIG. 16A, end effector (50) of instrument (10) is inserted into a proximal portion (313) of first channel (312). End effector (50) is oriented such that cover (52) of end effector (50) is up. As shown in FIG. 16B, end effector (50) is further distally inserted into first channel (312) along a longitudinal axis defined by first channel (312) until cover (52) of end effector (50) contacts engagement feature (314) of sliding member (320). Sliding member (320) is then moved in a proximal direction along the longitudinal axis defined by first channel (312).

Figure 16C:
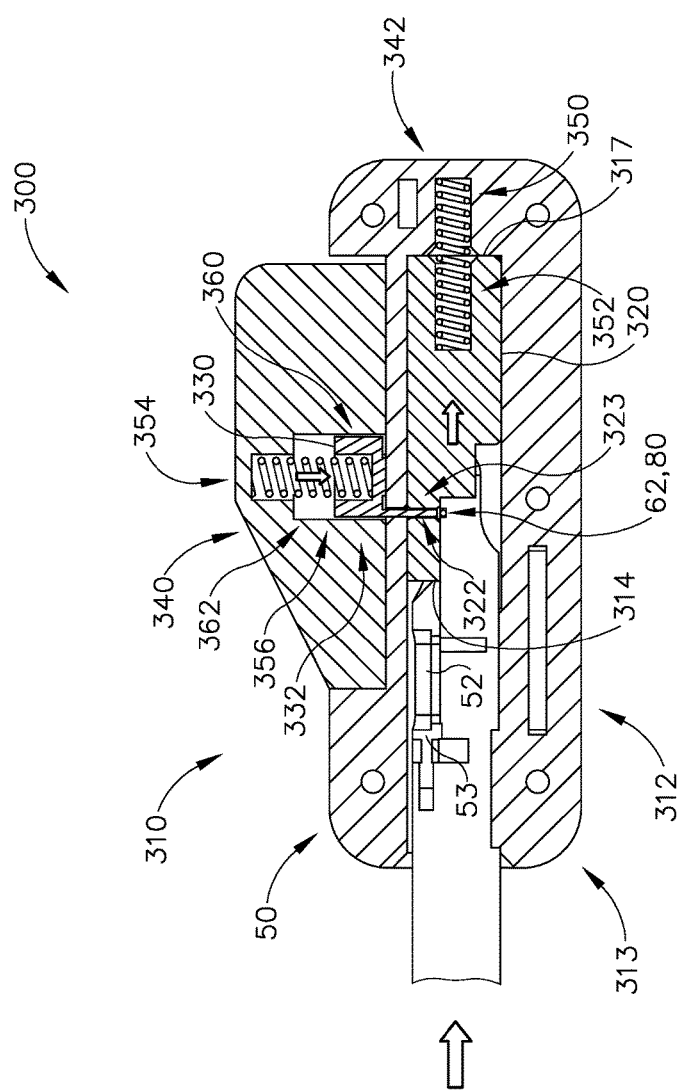
FIG. 16C depicts a side cross sectional view, taken along line 16-16 of FIG. 14, of the suturing instrument of FIG. 1 receiving a needle from the needle loader of FIG. 14.
Figure 16D:
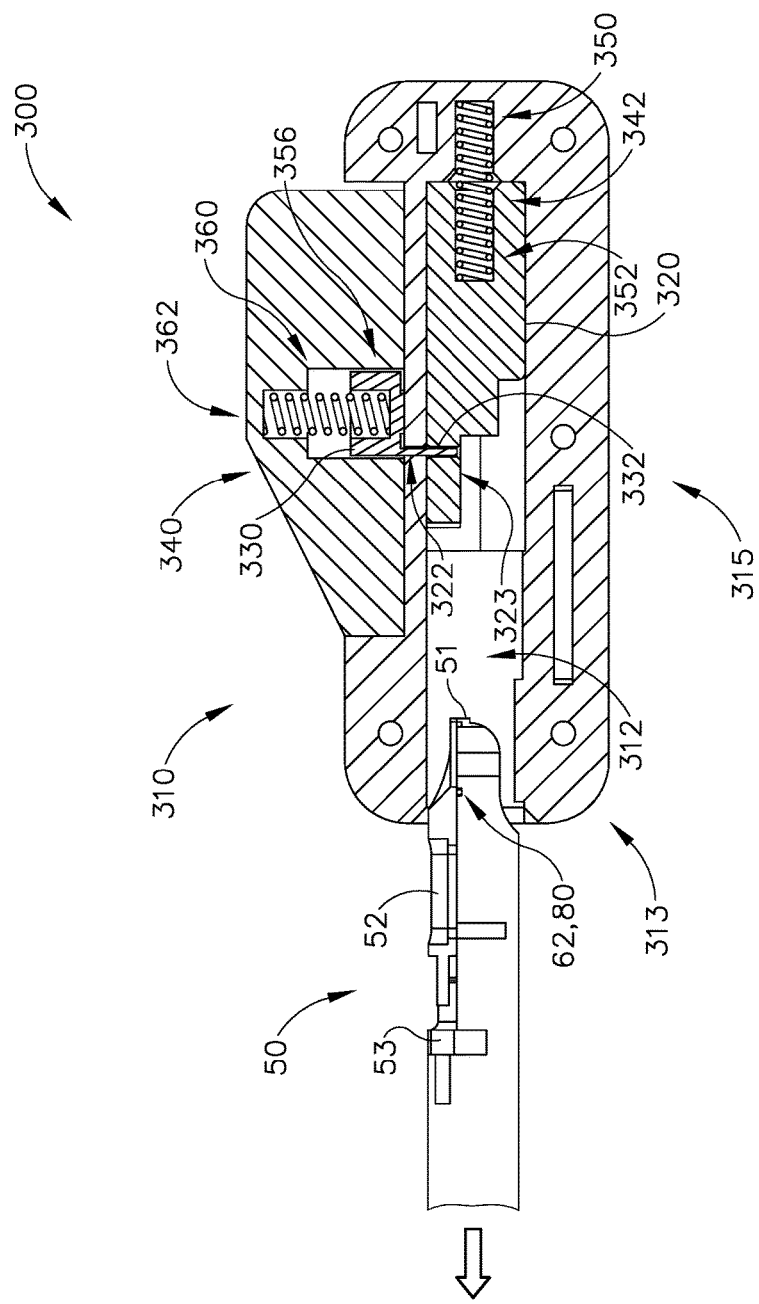
FIG. 16D depicts a side cross sectional view, taken along line 16-16 of FIG. 14, of the suturing instrument of FIG. 1 being removed from the needle loader of FIG. 14.
Figure 17:
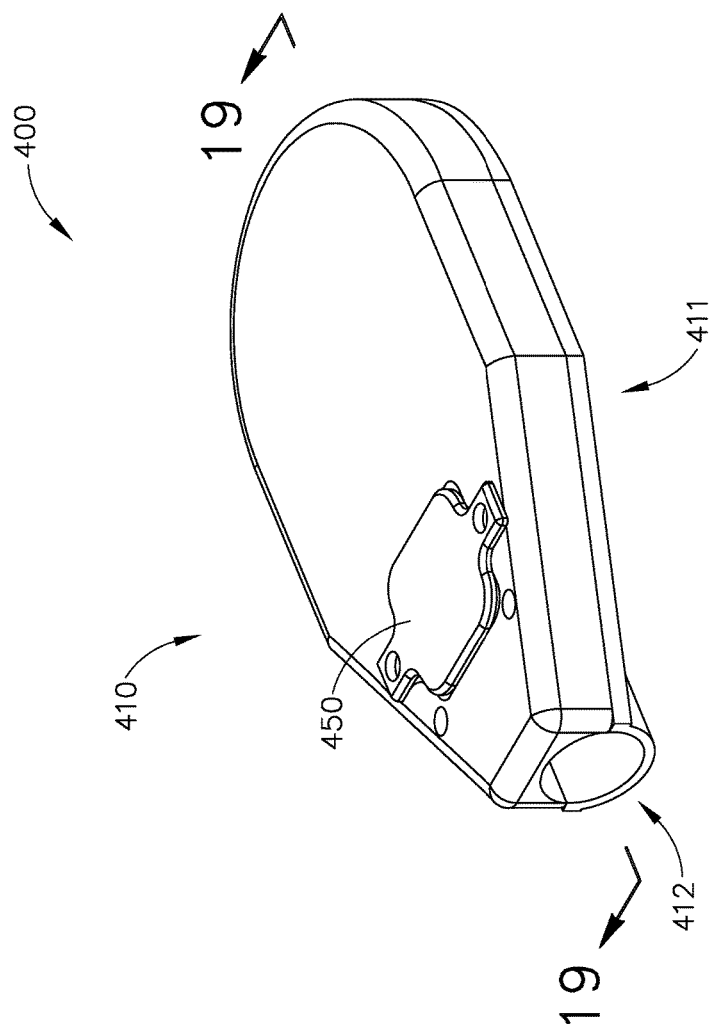
FIG. 17 depicts a perspective view of another exemplary alternative needle loader suitable for use with the instrument of FIG. 1.

As shown in FIG. 16C, end effector (50) is then driven further distally into first channel (312) along a longitudinal axis defined by first channel (312) until a distal end of sliding member (320) contacts a distal wall (317) of first channel (312) such that end effector (50) cannot be further inserted into first channel (312). As a result of driving sliding member (320) further into first channel (312), first spring (342) becomes compressed and exerts an increasing distally directed force upon sliding member (320). This force causes engagement feature (314) of sliding member (320) to drive cover (52) in a proximal direction. Once the distal end of sliding member (320) contacts distal wall (317) engagement feature (314) will have driven cover (52) in a proximal direction so that curved channel (62) is completely exposed and aligns with second needle-shaped opening (323) of sliding member (320). Also as a result of driving sliding member (320) further into first channel (312), first needle-shaped opening (322) of body (310) and second needle-shaped opening (323) of sliding member (320) align as shown in FIG. 16C. At this point, the top surface of sliding member (320) no longer counteracts the downward force from second spring (340), and drive member (330) and consequently needle (80) are driven downwardly through both needle-shaped openings (322, 323) and needle (80) is thereby deposited into curved channel (62). As shown in FIG. 16D, as end effector (50) is removed from first channel (312), cover (52) returns to its original position under the resilient bias of a spring in end effector (50), because cover (52) is no longer being driven by engagement feature (314).

Once end effector (50) is completely removed from needle loader (300), instrument (10) is ready for use. It should be noted that needle loader (300) may further comprise suturing thread within body (310), such that the suturing thread is spooled about an internal or external portion of body (310). Such suturing thread may be already secured to needle (80), such that the operator will pull suturing thread from body (310) as the operator pulls the loaded end effector (50) away from body (310). However, body (310) need not comprise suturing thread. By way of example only, suturing thread may be provided as a separate component of needle loader (300).

D. Fourth Exemplary Automated Needle Loader

Figure 18:
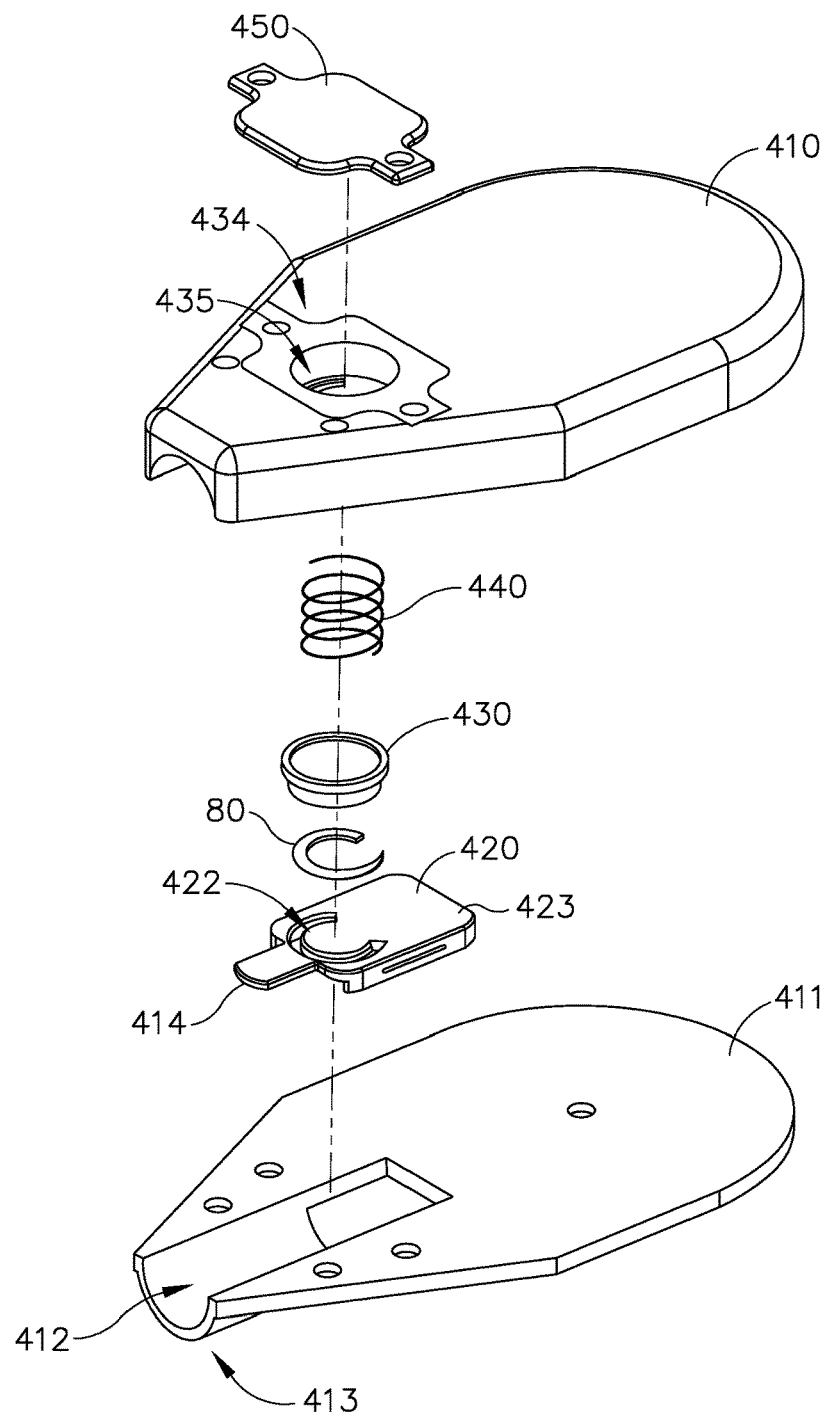
FIG. 18 depicts an exploded perspective view of the needle loader of FIG. 17.

FIGS. 17-19C show another exemplary alternative needle loader (400) that may be used to load a needle (80) in end effector (50). Needle loader (400) of this example comprises a cover (410), a base (411), a sliding member (420), a drive member (430), a spring (440), a cap (450), and needle (80). Cover (410) and base (411) together define a first channel (412) and a second channel (416). First channel (412) is configured to receive end effector (50) of instrument (10). Sliding member (420) is slidably disposed within second channel (416). As seen in FIG. 18, sliding member (420) comprises a first needle-shaped opening (422) and an engagement feature (414). Cover (410) presents a third channel (434). A bottom surface of third channel (434) presents a second needle-shaped opening (435). Cap (450) is secured to cover (410) such that cap (450) closes off an upper portion of third channel (434). Drive member (430) is slidably disposed within third channel (434). Drive member (430) comprises a downardly oriented needle-shaped protrusion (432). Drive member (430) is oriented such that needle-shaped protrusion (432) aligns with second needle-shaped opening (435). Needle (80) is disposed within second needle-shaped opening (435) and needle-shaped protrusion (432) of drive member (430) rests upon needle (80). Spring (440) is disposed within third channel (434) between drive member (430) and cap (450) such that spring (440) exerts a downward force upon drive member (430) and consequently needle (80). This downward force is counteracted by a force from a top surface (423) of sliding member (420).

Figure 19A:
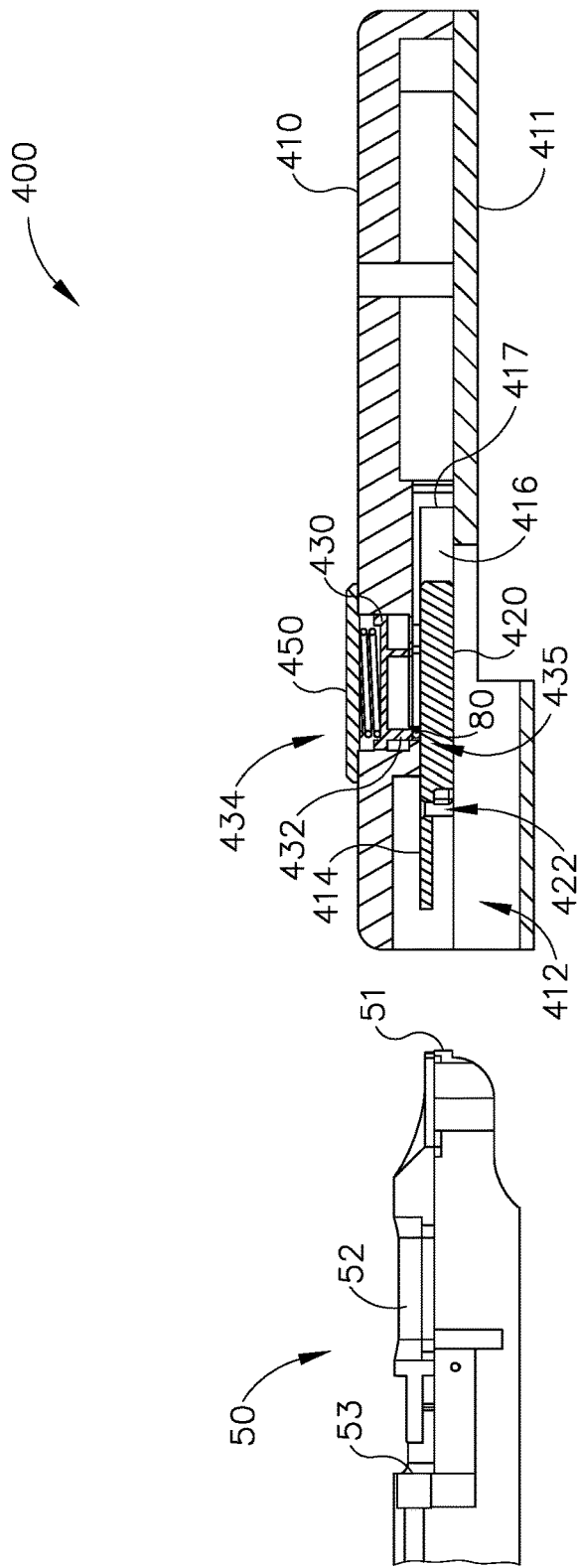
FIG. 19A depicts a side cross sectional view, taken along line 19-19 of FIG. 17, of the suturing instrument of FIG. 1 being inserted into the needle loader of FIG. 17.

In an exemplary use, needle loader (400) is used to insert needle (80) into curved channel (62) of end effector (50). As shown in FIG. 19A, end effector (50) of instrument (10) is inserted into a proximal portion (413) of first channel (412).

Figure 19B:
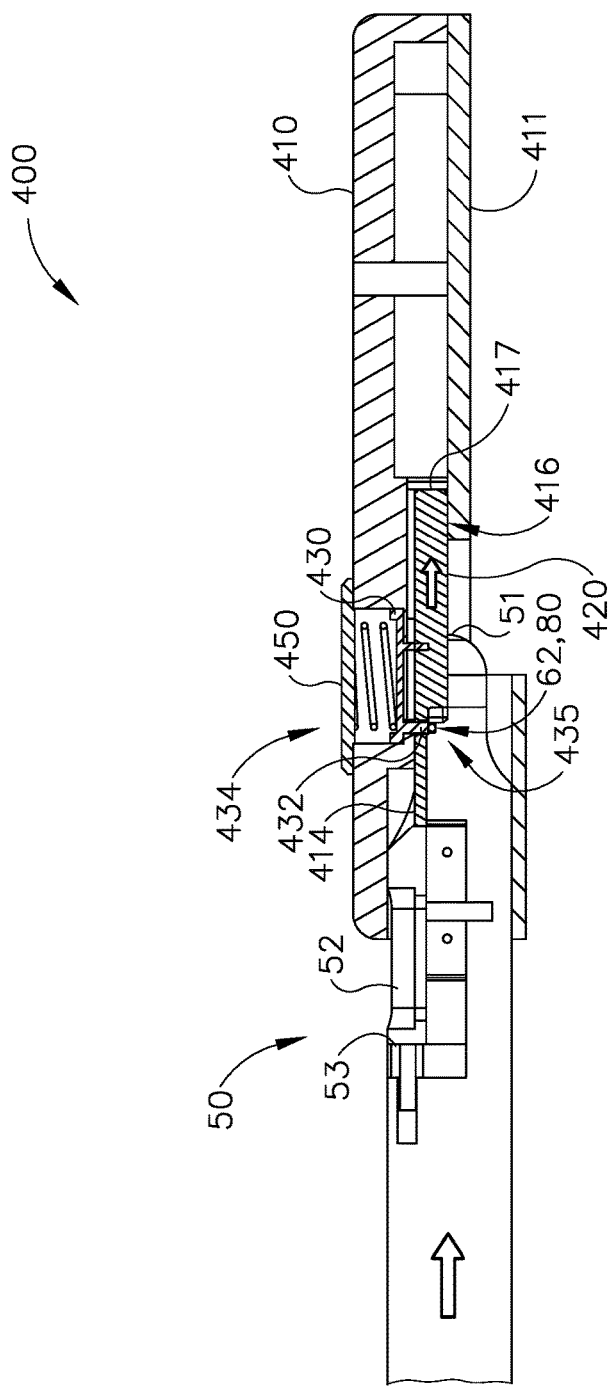
FIG. 19B depicts a side cross sectional view, taken along line 19-19 of FIG. 17, of an engagement feature of the needle loader of FIG. 17 engaging a cover of the suturing instrument of FIG. 1, and the suturing instrument of FIG. 1 receiving a needle from the needle loader of FIG. 17.

End effector (50) is oriented such that cover (52) of end effector (50) is up. As shown in FIG. 19B, end effector (50) is inserted into first channel (412) along a longitudinal axis defined by first channel (412) until cover (52) of end effector (50) contacts engagement feature (414) of sliding member (420). Sliding member (420) is then moved in a proximal direction within second channel (416).

Figure 19C:
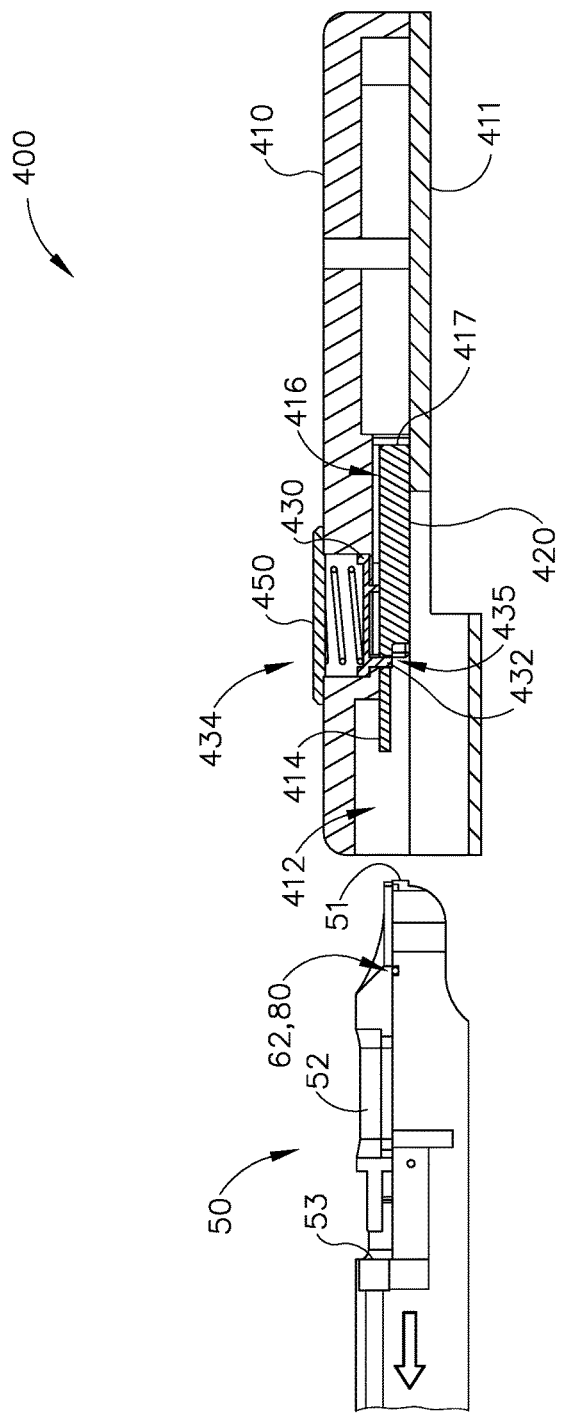
FIG. 19C depicts a side cross sectional view, taken along line 19-19 of FIG. 17, of the suturing instrument of FIG. 1 being removed from the needle loader of FIG. 17.

As shown in FIG. 19B, end effector (50) is then driven further distally into first channel (412) along a longitudinal axis defined by first channel (412) until a distal end of sliding member (420) contacts a distal wall (417) of second channel (416) such that sliding member (420) cannot be driven further distally into second channel (416). As end effector (50) is driven further distally into first channel (412), cover (52) is concurrently driven in a proximal direction until a proximal end of cover (52) contacts a proximal wall (53) of end effector (50) such that neither cover (52) nor end effector (50) can be moved further. At this point, engagement feature (414) will have driven cover (52) in a proximal direction so that curved channel (62) is completely exposed and aligns with first needle-shaped opening (422) of sliding member (420). Also as a result of driving sliding member (20) further distally into second channel (416), second needle-shaped opening (435) of cover (410) and first needle-shaped opening (422) of sliding member (420) align as shown in FIG. 19B. At this point, the top surface of sliding member (420) no longer counteracts the downward force from spring (440) and drive member (430) and consequently needle (80) are driven downwardly through both needle-shaped openings (422, 435) and needle (80) is deposited into curved channel (62). As shown in FIG. 19C, as end effector (50) is removed from first channel (412), cover (52) returns to its original position under the resilient bias of a spring in end effector (50), because cover (52) is no longer being driven by engagement feature (414).

Once end effector (50) is completely removed from needle loader (400), instrument (10) is ready for use. It should be noted that needle loader (400) may further comprise suturing thread within body (410), such that the suturing thread is spooled about an internal or external portion of body (410). Such suturing thread may be already secured to needle (80), such that the operator will pull suturing thread from body (410) as the operator pulls the loaded end effector (50) away from body (410). However, body (410) need not comprise suturing thread. By way of example only, suturing thread may be provided as a separate component of needle loader (400).

III. Miscellaneous

Any of the needle loaders (100, 200, 300, 400) described herein may include one or more features that provide audible, visual, and/or tactile feedback indicating that a needle (80) has been successfully loaded in end effector (50). Various suitable forms that such feedback features may take will be apparent to those of ordinary skill in the art in view of the teachings herein. In addition, any of the needle loaders (100, 200, 300, 400) described herein may include various poka-yoke features configured to ensure that end effector (50) is inserted into needle loader (100, 200, 300, 400) at the appropriate orientation and depth, etc. Various suitable forms that such poka-yoke features may take will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

While terms such as "clockwise" and "counterclockwise" have been used to describe directions of rotational movement during exemplary uses of instruments, it should be understood that these specific rotational directions are being provided only in reference to the examples depicted in the drawings. It is contemplated that rotational movement may be provided in directions opposite to those used above. Therefore, use of the terms "clockwise" and "counterclockwise" in any examples described herein should not be viewed as limiting in any way.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. In addition or in the alternative, various teachings herein may be readily combined with various teachings in U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; and/or U.S. Pat. No. 7,824,401, entitled "Surgical Tool With Writed Monopolar Electrosurgical End Effectors," issued Nov. 2, 2010, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body including:
      (i) a body channel extending therethrough to a distal end, the body channel configured to receive a surgical instrument,
      (ii) a hole in communication with the body channel, and
      (iii) an engagement feature extending into the body channel, the engagement feature configured to engage a movable cover of the surgical instrument and direct movement of the movable cover of the surgical instrument as the surgical instrument is received within the body channel for uncovering a needle channel of the surgical instrument;
   (b) a needle releasably secured relative to the body within the hole; and
   (c) a drive member positioned in the body and extending into the body channel, the drive member configured to selectively move from a first drive position to a second drive position upon receiving the surgical instrument thereagainst, wherein selectively moving the drive member from the first drive position toward the second drive position is configured to release the needle from the hole and into the body channel for inserting the needle into the needle channel of the surgical instrument received within the body channel.

2. The apparatus of claim 1, wherein the body channel extends through the body in a generally longitudinal direction, and wherein the drive member is configured to move generally longitudinally from the first drive position to the second drive position.

3. The apparatus of claim 1, wherein the drive member is configured to pivot about a pivot member from the first drive position to the second drive position.

4. The apparatus of claim 2, wherein the drive member is connected to the pivot member via an arm extending therebetween, wherein the body includes a cavity and an opening extending between the cavity and the body channel, and wherein the pivot member is positioned within the cavity and the drive member extends from the arm, through the opening, and into the body channel.

5. The apparatus of claim 3, wherein the arm is positioned against a distal wall of the cavity when the drive member is in the second drive position such that the distal wall is configured to halt further distal movement of the drive member.

6. The apparatus of claim 1, wherein the drive member is operatively connected to an arm such that the drive member is configured to move the arm from a first arm position toward a second arm position, wherein moving the drive member from the first drive position toward the second drive position respectively moves the arm from the first arm position toward the second arm position, and wherein the arm contacts the needle as the arm moves from the first arm position toward the second arm position to thereby release the needle from the hole and into the channel.

7. The apparatus of claim 6, wherein the body channel extends through the body in a generally longitudinal direction, wherein the hole intersects the body channel in a generally transverse direction, and wherein the needle is configured to be released from the hole into the body channel in the generally transverse direction.

8. The apparatus of claim 7, wherein the arm is configured to move generally transversely from the first arm position to the second arm position.

9. The apparatus of claim 8, wherein the arm extends from a pivot member such that the arm is configured to pivot from the first arm position toward the second arm position.

10. The apparatus of claim 1, further comprising a first arm projecting relative to a second arm, wherein the drive member extends from the first arm, wherein the drive member is configured to move the second arm via the first arm from a first arm position toward a second arm position, wherein moving the drive member from the first drive position toward the second drive position respectively moves the second arm from the first arm position toward the second arm position, and wherein the second arm contacts the needle as the second arm moves from the first arm position toward the second arm position to thereby release the needle from the hole and into the body channel.

11. The apparatus of claim 10, further comprising a lever, wherein the lever includes the first arm and the second arm.

12. The apparatus of claim 11, wherein the lever further includes a pivot member and the first and second arms extend from the pivot member such that the first and second arms are configured to pivot about the pivot member, wherein the drive member pivots from the first drive position toward the second drive position, and wherein the second arm pivots from the first arm position toward the second arm position.

13. The apparatus of claim 12, wherein the body channel extends through the body in a generally longitudinal direction, wherein the hole intersects the body channel in a generally transverse direction, and wherein the needle is configured to be released from the hole into the body channel in the generally transverse direction.

14. The apparatus of claim 13, wherein the drive member pivots generally longitudinally in the distal direction from the first drive position toward the second drive position, and wherein the second arm pivots generally transversely from the first arm position toward the second arm position.

15. The apparatus of claim 1, wherein the engagement feature defines an engagement width, wherein the body channel defines a channel width, and wherein the engagement width is less than the channel width.

16. An apparatus, comprising:
   (a) a body including:
      (i) a body channel extending therethrough to a distal end, the body channel configured to receive a surgical instrument,
      (ii) a hole in communication with the body channel, wherein the hole is configured to have a needle releasably secured therein, and
      (iii) an engagement feature extending into the body channel, the engagement feature configured to engage a movable cover of the surgical instrument and direct movement of the movable cover of the surgical instrument as the surgical instrument is received within the body channel for uncovering a needle channel of the surgical instrument; and
   (b) a drive member positioned in the body and extending into the body channel, the drive member configured to selectively move from a first drive position to a second drive position upon receiving the surgical instrument thereagainst, wherein selectively moving the drive member from the first drive position toward the second drive position releases the needle from the hole into the body channel and inserts the needle into the needle channel of the surgical instrument received within the body channel.

17. The apparatus of claim 16, wherein the body channel extends through the body in a generally longitudinal direction, wherein the hole intersects the body channel in a generally transverse direction.

18. A method of inserting a needle into a needle channel of a surgical instrument with an apparatus, wherein the apparatus comprises (a) a body including: (i) a body channel extending therethrough to a distal end, the body channel configured to receive a surgical instrument, (ii) a hole in communication with the body channel, and (iii) an engagement feature extending into the body channel, the engagement feature configured to engage a movable cover of the surgical instrument and direct movement of the movable cover of the surgical instrument as the surgical instrument is received within the body channel for uncovering a needle channel of the surgical instrument; (b) a needle releasably secured relative to the body within the hole; and (c) a drive member positioned in the body and extending into the body channel, the drive member configured to selectively move from a first drive position to a second drive position upon receiving the surgical instrument thereagainst, wherein selectively moving the drive member from the first drive position toward the second drive position is configured to release the needle from the hole and into the body channel for inserting the needle into the needle channel of the surgical instrument received within the body channel, the method comprising:
   (a) inserting the surgical instrument along a longitudinal axis into the body channel of the body;
   (b) engaging the engagement feature positioned within the body against the cover of the surgical instrument as the surgical instrument moves distally along the longitudinal axis such that the engagement feature directs the cover proximally relative to a remainder of the surgical instrument thereby uncovering the needle channel;
   (c) aligning the hole within the body with the uncovered needle channel, wherein the hole has the needle releasably secured therein; and
   (b) moving the drive member distally from the first drive position toward the second drive position with the surgical instrument thereby releasing the needle from the hole and into the needle channel.

19. The method of claim 18 wherein moving the drive member further includes pivoting the drive member distally from the first drive position toward the second drive position.

20. The method of claim 18 wherein moving the drive member simultaneously occurs while engaging the engagement feature.

* * * * *